(12) United States Patent
Tak et al.

(10) Patent No.: US 12,174,180 B2
(45) Date of Patent: Dec. 24, 2024

(54) FLUID TEST CARTRIDGE, FLUID TEST APPARATUS INCLUDING THE SAME, AND METHOD FOR CONTROLLING THE FLUID TEST APPARATUS

(71) Applicant: PRECISION BIOSENSOR INC., Daejeon (KR)

(72) Inventors: Yu Kyung Tak, Seoul (KR); Sung Ha Park, Hwaseong-si (KR); Takayuki Taguchi, Osaka (JP)

(73) Assignee: PRECISION BIOSENSOR INC., Daejeon (KR)

( * ) Notice: Subject to any disclaimer, the term of this patent is extended or adjusted under 35 U.S.C. 154(b) by 929 days.

(21) Appl. No.: 16/144,533

(22) Filed: Sep. 27, 2018

(65) Prior Publication Data

US 2019/0310247 A1  Oct. 10, 2019

(30) Foreign Application Priority Data

Apr. 6, 2018  (KR) .................. 10-2018-0040265

(51) Int. Cl.
*G01N 33/543* (2006.01)
*G01N 21/77* (2006.01)
(Continued)

(52) U.S. Cl.
CPC ....... *G01N 33/54346* (2013.01); *G01N 21/77* (2013.01); *G01N 33/5306* (2013.01);
(Continued)

(58) Field of Classification Search
CPC ............. G01N 33/54386; G01N 21/77; G01N 33/5306; G01N 33/54346; G01N 33/552;
(Continued)

(56) References Cited

U.S. PATENT DOCUMENTS 4,455,377 A  6/1984 Finnerty et al.
6,242,267 B1 * 6/2001 Herron ............. G01N 33/54373
                                                435/7.5
(Continued)

FOREIGN PATENT DOCUMENTS

CN  107543933 A  1/2018
EP  2 560 005 A1  2/2013
(Continued)

OTHER PUBLICATIONS

Agasti SS, Rana S, Park MH, Kim CK, You CC, Rotello VM. Nanoparticles for detection and diagnosis. Adv Drug Deliv Rev. Mar. 8, 2010;62(3):316-28. doi: 10.1016/j.addr.2009.11.004. Epub Nov. 11, 2009. PMID: 19913581; PMCID: PMC2827652. (Year: 2010).*

(Continued)

*Primary Examiner* — Christopher L Chin
*Assistant Examiner* — Christina Lusi
(74) *Attorney, Agent, or Firm* — LEX IP MEISTER, PLLC

(57) ABSTRACT

A fluid test cartridge, a fluid test apparatus, and a method for controlling the same. The fluid test apparatus includes a housing, and a fluid test cartridge that is accommodated in the housing. The fluid test cartridge includes at least one chamber in which a fluid sample to be tested and a drying reagent can be accommodated. The fluid test apparatus includes a light emitter configured to emit light to the at least one chamber, a light sensor, and a processor configured to detect a concentration of a first material in the fluid sample. The drying reagent includes a non-metallic particle bound to a second material that specifically binds to the first material. Tests can thus be carried out over a wider range of wavelengths, and testing errors can be reduced.

11 Claims, 21 Drawing Sheets

(51) Int. Cl.
*G01N 21/82* (2006.01)
*G01N 33/53* (2006.01)
*G01N 33/552* (2006.01)

(52) U.S. Cl.
CPC ... *G01N 33/552* (2013.01); *G01N 2021/7786* (2013.01); *G01N 2021/825* (2013.01)

(58) Field of Classification Search
CPC ..... G01N 2021/7786; G01N 2021/825; G01N 21/78; G01N 2021/0325; G01N 21/85; G01N 21/27; G01N 33/487; G01N 35/00; G01N 21/274; G01N 33/4875; G01N 35/00623; B01L 2200/025; B01L 2200/143; B01L 2300/0654; B01L 2300/0816; B01L 2300/0864; B01L 3/502715; A61B 5/00; A61B 5/0059
USPC ............ 435/7.1, 287.1, 287.2, 288.2, 288.3, 435/288.4, 288.5, 288.7; 356/246
See application file for complete search history.

(56) References Cited

U.S. PATENT DOCUMENTS

| | | | |
|---|---|---|---|
| 7,172,804 B2* | 2/2007 | Kelso .................. | B01J 19/0046 435/7.1 |
| 2002/0015958 A1* | 2/2002 | Audeh .................. | B82Y 30/00 436/518 |
| 2009/0208975 A1* | 8/2009 | D'Costa .............. | G01N 33/558 435/287.7 |
| 2009/0286327 A1 | 11/2009 | Cho et al. | |
| 2010/0009431 A1 | 1/2010 | Cho et al. | |
| 2011/0003710 A1* | 1/2011 | Konstantopoulos ..... | B82Y 5/00 506/9 |
| 2011/0014630 A1 | 1/2011 | Sun, Jr. | |
| 2011/0143364 A1 | 6/2011 | Kim et al. | |
| 2012/0309636 A1 | 12/2012 | Gibbons et al. | |
| 2014/0295468 A1 | 10/2014 | Kasagi et al. | |
| 2015/0093760 A1 | 4/2015 | Kim et al. | |
| 2015/0160206 A1* | 6/2015 | Park ................. | G01N 33/54366 435/287.2 |
| 2015/0260709 A1 | 9/2015 | Shimayama et al. | |
| 2015/0338387 A1* | 11/2015 | Ehrenkranz ............ | A61K 31/12 436/501 |
| 2016/0310948 A1 | 10/2016 | Nowakowski et al. | |
| 2017/0016829 A1* | 1/2017 | Swihart .............. | G01N 21/6454 |

FOREIGN PATENT DOCUMENTS

| | | |
|---|---|---|
| EP | 3301432 A1 | 4/2018 |
| JP | H04-72569 A | 3/1992 |
| JP | 04504758 A | 8/1992 |
| JP | 2001-221799 A | 8/2001 |
| JP | 2007-114162 A | 5/2007 |
| JP | 2009-513798 A | 4/2009 |
| JP | 2011-527753 A | 11/2011 |
| JP | 2012523571 A | 10/2012 |
| JP | 2013513794 A | 4/2013 |
| JP | 5348901 B2 | 11/2013 |
| JP | 2015-072249 A | 4/2015 |
| JP | 2016-197106 A | 11/2016 |
| JP | 2018-44920 A | 3/2018 |
| JP | 2018044920 A | 3/2018 |
| KR | 10-2009-0064942 A | 6/2009 |
| KR | 10-2009-0118749 A | 11/2009 |
| KR | 10-2015-0067637 A | 6/2015 |
| KR | 10-2017-0065246 A | 6/2017 |
| KR | 10-2017-0139157 A | 12/2017 |
| WO | 2009128209 A1 | 10/2009 |
| WO | 2011/129220 A1 | 10/2011 |

OTHER PUBLICATIONS

Communication dated Feb. 22, 2021, issued by the Japanese Patent Office in Japanese Application No. 2018-535131.
Communication dated Sep. 14, 2020, issued by the Japanese Patent Office in Japanese Application No. 2018-535131.
International Search Report (PCT/ISA/210) dated Feb. 11, 2019, issued by the International Searching Authority in counterpart International Application No. PCT/KR2018/006032.
Communication dated Mar. 30, 2020, issued by the Japanese Patent Office in Japanese Application No. 2018-535131.
Decision of Refusal communication dated Jul. 19, 2021 issued by the Japanese Patent Office in Japanese Application No. 2018-535131.
Decision of Dismissal of Amendment communication dated Jul. 19, 2021 issued by the Japanese Patent Office in Japanese Application No. 2018-535131.

* cited by examiner

101a

101b

101c

101d

101e

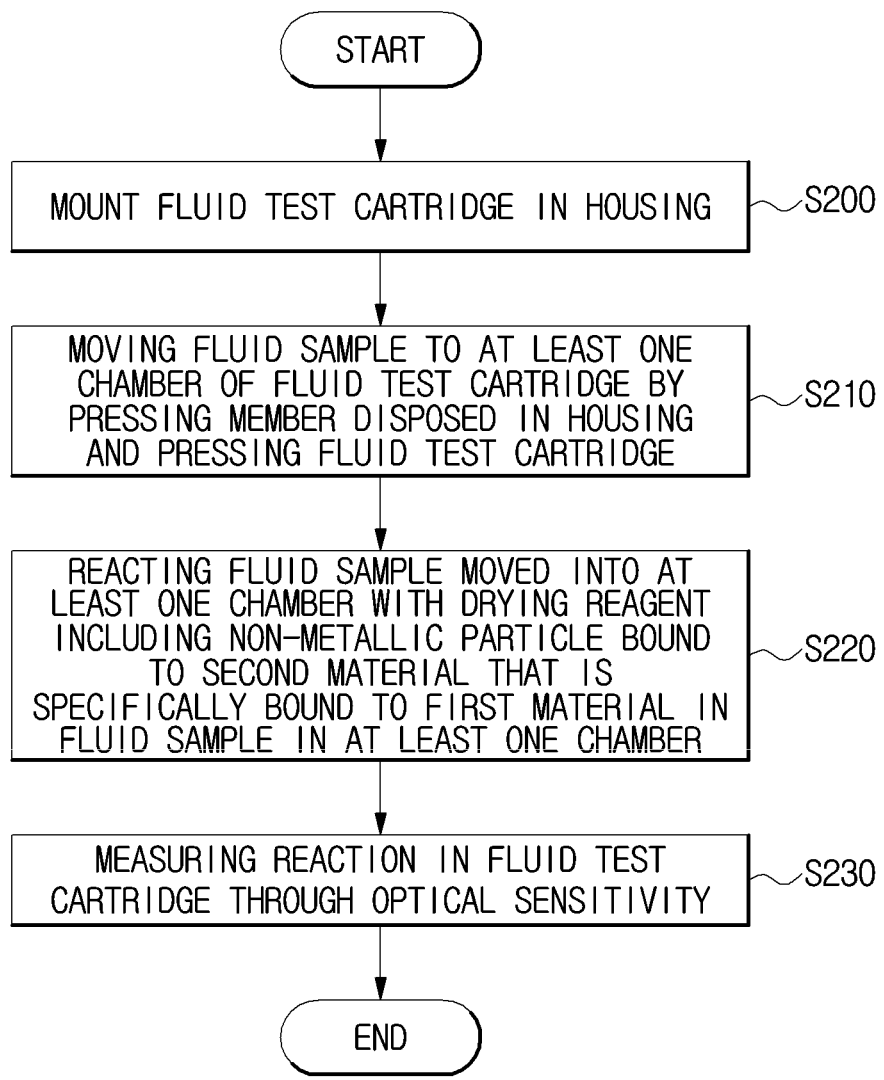

FLUID TEST CARTRIDGE, FLUID TEST APPARATUS INCLUDING THE SAME, AND METHOD FOR CONTROLLING THE FLUID TEST APPARATUS

CROSS-REFERENCE TO RELATED APPLICATION

The application is based on and claims priority under 35 U.S.C. § 119 to Korean Patent Application No. 10-2018-0040265, filed on Apr. 6, 2018, in the Korean Intellectual Property Office, the disclosure of which is incorporated by reference herein in its entirety.

BACKGROUND

1. Field

This disclosure relates to a fluid test cartridge, a fluid test apparatus including the same, and a method for controlling the fluid test apparatus.

2. Description of the Related Art

There is a need for an apparatus and a method for quickly and accurately testing substances in various fields, such as environmental monitoring, food inspection, and medical diagnosis. In the related art, in order to carry out a test according to a predetermined protocol, skilled technicians have to manually perform various operations, such as reagent injection, mixing, separation, transfer, reaction, centrifugation, etc. These manual operations have often caused errors in the testing results due to mistakes made by the experimenters.

In order to overcome this problem, miniaturized and automated instruments have been developed which can rapidly analyze test substances. For example, a portable fluid test cartridge can analyze fluid samples quickly in various locations. It is expected that future development will lead to portable fluid test cartridges being able to perform even more functions in additional fields. Also, research into precise analysis methods through miniaturized and automated instruments for analyzing fluid samples is ongoing and may lead to additional advances.

Analysis of a fluid sample is done by measuring the optical sensitivity of a target material in the fluid sample. However, depending on a type of reagent used for measuring the reaction of the fluid sample, there is a limitation on the measurement wavelength that can be used to perform the test, or the sensitivity of the reagent to the wavelength variation may limit the test.

SUMMARY

Provided are a fluid test cartridge, a fluid test apparatus, and a method for controlling the fluid test apparatus, which are capable of testing a fluid sample over a wider range of wavelengths.

According to an embodiment, a fluid test apparatus may comprise: a housing; a fluid test cartridge that is accommodated in the housing, the fluid test cartridge including at least one chamber configured to accommodate a fluid sample and a drying reagent; a light emitter configured to emit light towards the at least one chamber; a light sensor configured receive the light incident on the at least one chamber and to detect optical property of a first material included in the fluid sample based on the received light; and a processor configured to determine a concentration of the first material based on the optical property detected by the light sensor, wherein the drying reagent includes a non-metallic particle bound to a second material that specifically binds to the first material.

The non-metallic particle may comprise at least one of a monomer or a complex.

The non-metallic particle may be a nano-sized particle, and the nano-sized particle is at least one element selected from the group consisting of carbon nanoparticles, ceramic nanoparticles, and polymeric nanoparticles.

The ceramic nanoparticle may be at least one element selected from the group consisting of glass and nano-silica.

The polymeric nanoparticle may be at least one element selected from the group consisting of polymethyl methacrylate, polystyrene, cellulose, latex, hydrogel, and agarose.

The first material may be at least one element selected from the group consisting of antigens, DNA, RNA, oligosaccharides, peptides, small molecules, and proteins.

The second material may be at least one element selected from the group consisting of antibodies, oligonucleotides, and proteins.

The drying reagent may further comprise an activator for facilitating a reaction between the fluid sample and the drying reagent.

The at least one chamber may comprise a first chamber which accommodates a first drying reagent, and a second chamber which accommodates a second drying reagent.

The drying reagent may block an entire wavelength range of visible light.

The processor may be further configured to determine concentration values of the first material over a plurality of wavelength bands of light received by the light sensor.

According to yet another embodiment, a fluid test cartridge may comprise an inlet through which a fluid sample is introduced; a tester configured to receive the fluid sample from the inlet and to test the fluid sample, wherein the tester comprises at least one chamber that accommodates the fluid sample introduced through the inlet a drying reagent, the drying reagent including a non-metallic particle bound to a second material that specifically binds to a first material included in the fluid sample.

The non-metallic particle may comprise at least one of a monomer or a complex.

The non-metallic particle may be a nano-sized particle, and is at least one element selected from the group consisting of carbon nanoparticles, ceramic nanoparticles, polymeric nanoparticles.

The ceramic nanoparticle may be at least one element selected from the group consisting of glass and nano-silica.

The polymeric nanoparticle is at least one element selected from the group consisting of polymethyl methacrylate, polystyrene, cellulose, latex, hydrogel, and agarose.

The first material in the fluid sample may be at least one element selected from the group consisting of antigens, DNA, RNA, oligosaccharides, peptides, small molecules, and proteins.

The second material may be at least one element selected from the group consisting of antibodies, oligonucleotides, and proteins.

According to yet another embodiment, a method for controlling a fluid test apparatus includes a fluid test cartridge including at least one chamber configured to accommodate a fluid sample to be tested, and a detector configured to detect a reaction in the fluid test cartridge, the method comprising: mounting the fluid test cartridge in a housing of the fluid test apparatus; reacting the fluid sample accommodated in the at least one chamber with a drying reagent accommodated in the at least one chamber, the drying reagent including a non-metallic particle bound to a second material that specifically binds to a first material in the fluid sample; and analyzing a reaction in the fluid test cartridge by measuring an optical property of the first material with the detector.

The at least one chamber may include a first chamber accommodating a first drying reagent, and a second chamber accommodating a second drying reagent, and the analyzing may comprise measuring a first optical property in the first chamber with the detector, and measuring a second optical property in the second chamber with the detector.

BRIEF DESCRIPTION OF THE DRAWINGS

The above and other aspects, features, and advantages of certain embodiments of the present disclosure will be more apparent from the following description taken in conjunction with the accompanying drawings, in which:

FIG. 13 is a flow chart showing a method for controlling a fluid test apparatus according to an embodiment.

DETAILED DESCRIPTION

Hereinafter, embodiments of the disclosure will be described in detail with reference to the accompanying drawings. As used herein, expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Figure 1:
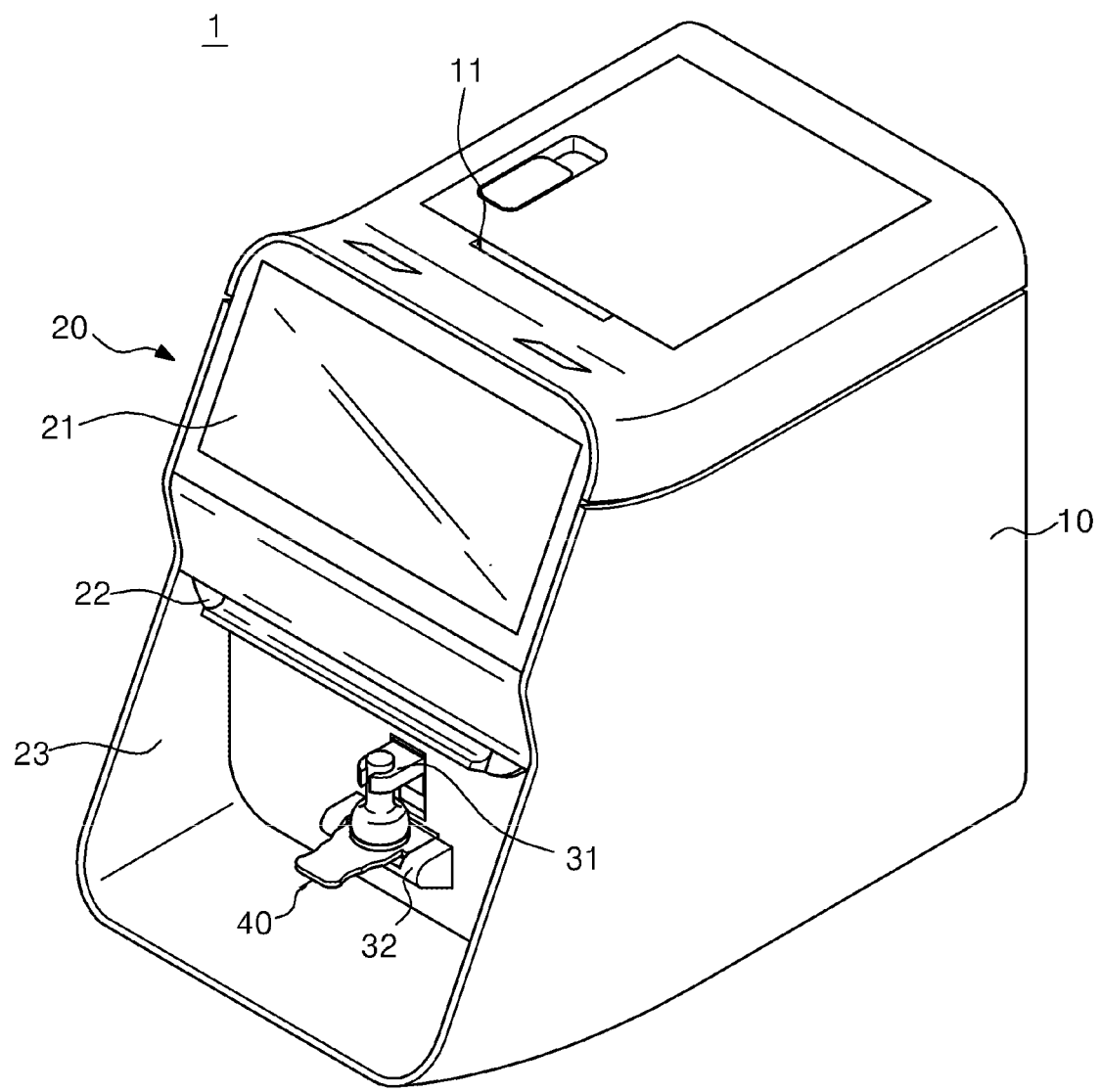
FIG. 1 shows a fluid test apparatus to which a fluid test cartridge is coupled, according to an embodiment.
Figure 2:
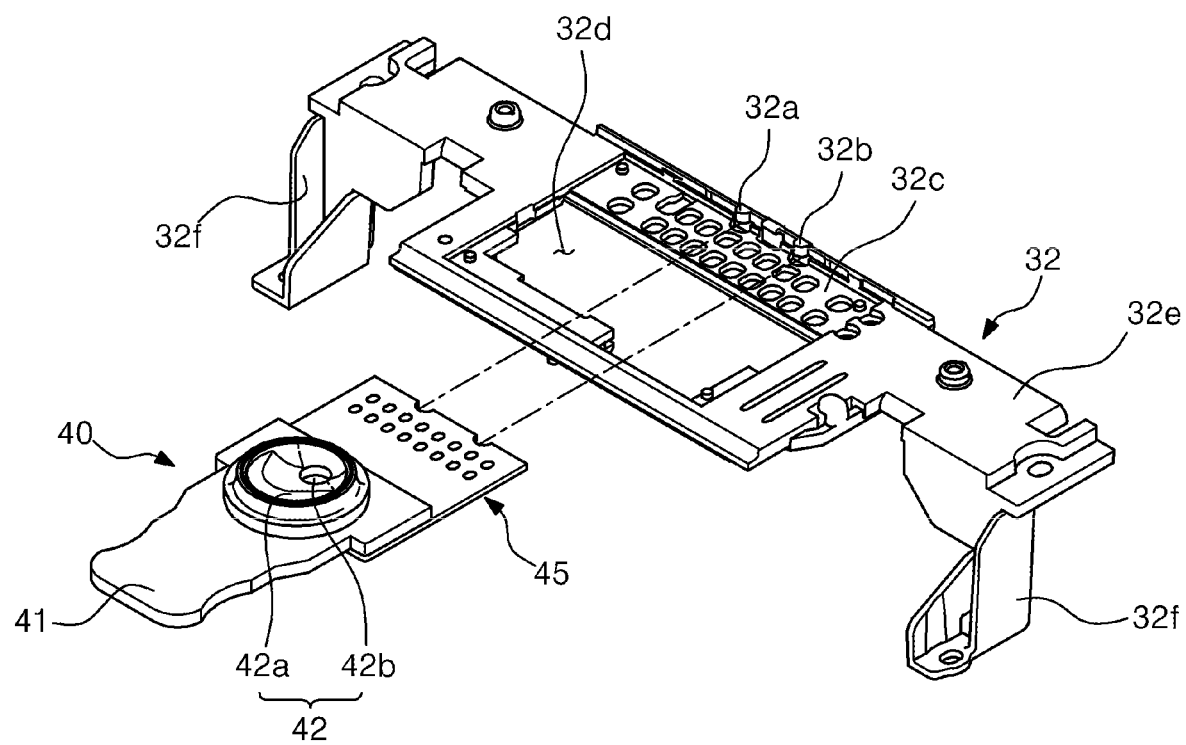
FIG. 2 is an exploded perspective view of the fluid test cartridge according to an embodiment and a mounting member of the fluid test apparatus to which the fluid test cartridge is coupled.
Figure 3:
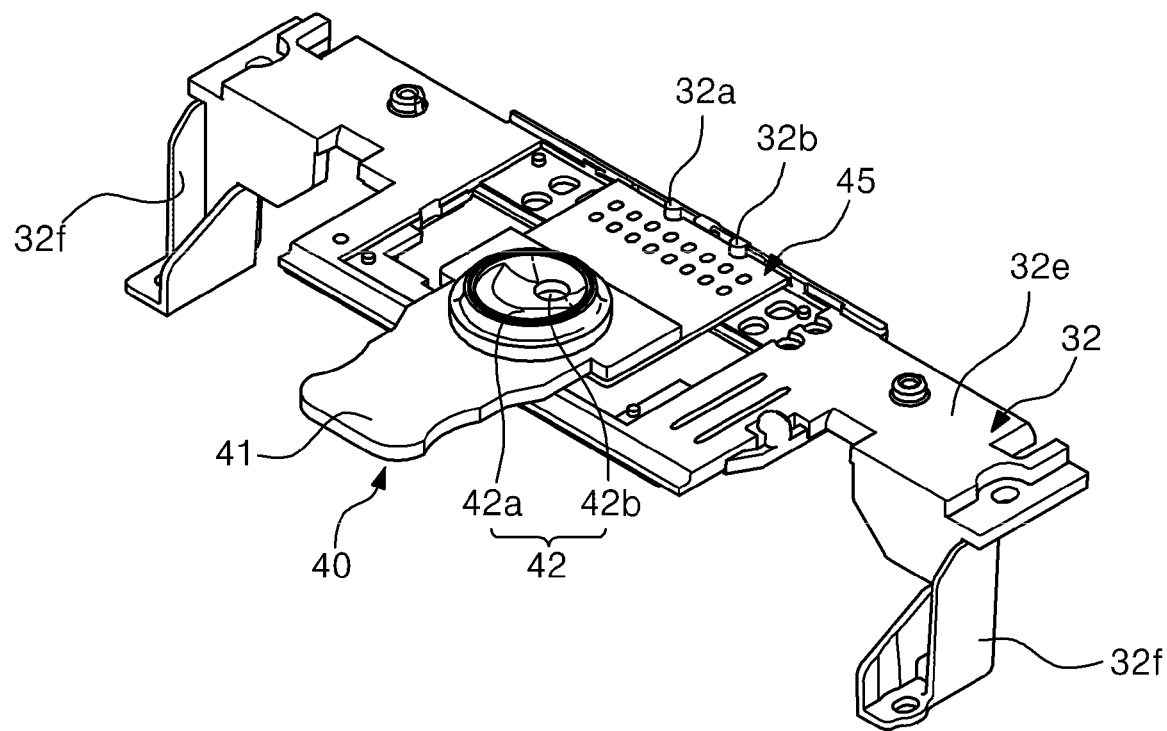
FIG. 3 shows a state in which the fluid test cartridge according to an embodiment is coupled to the mounting member of the fluid test apparatus.
Figure 4:
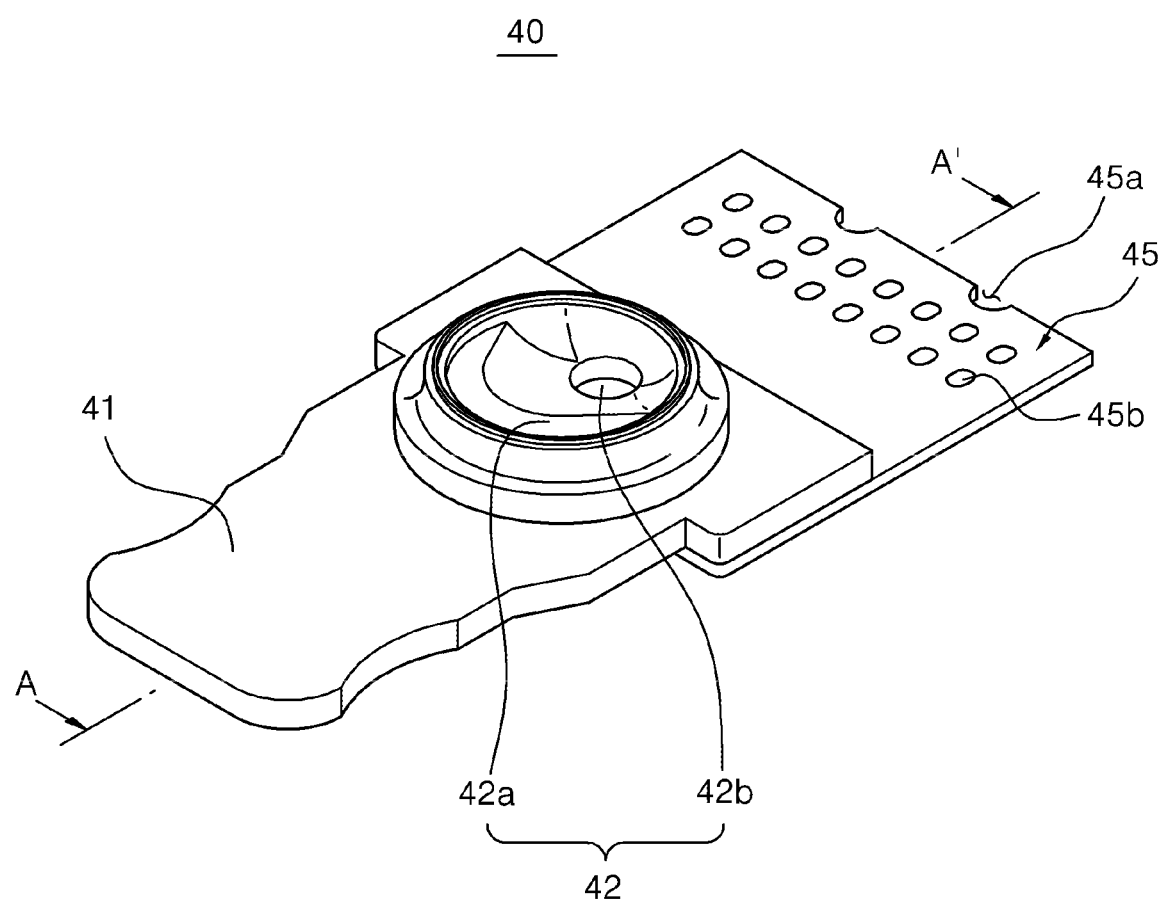
FIG. 4 shows the fluid test cartridge according to an embodiment.
Figure 5:
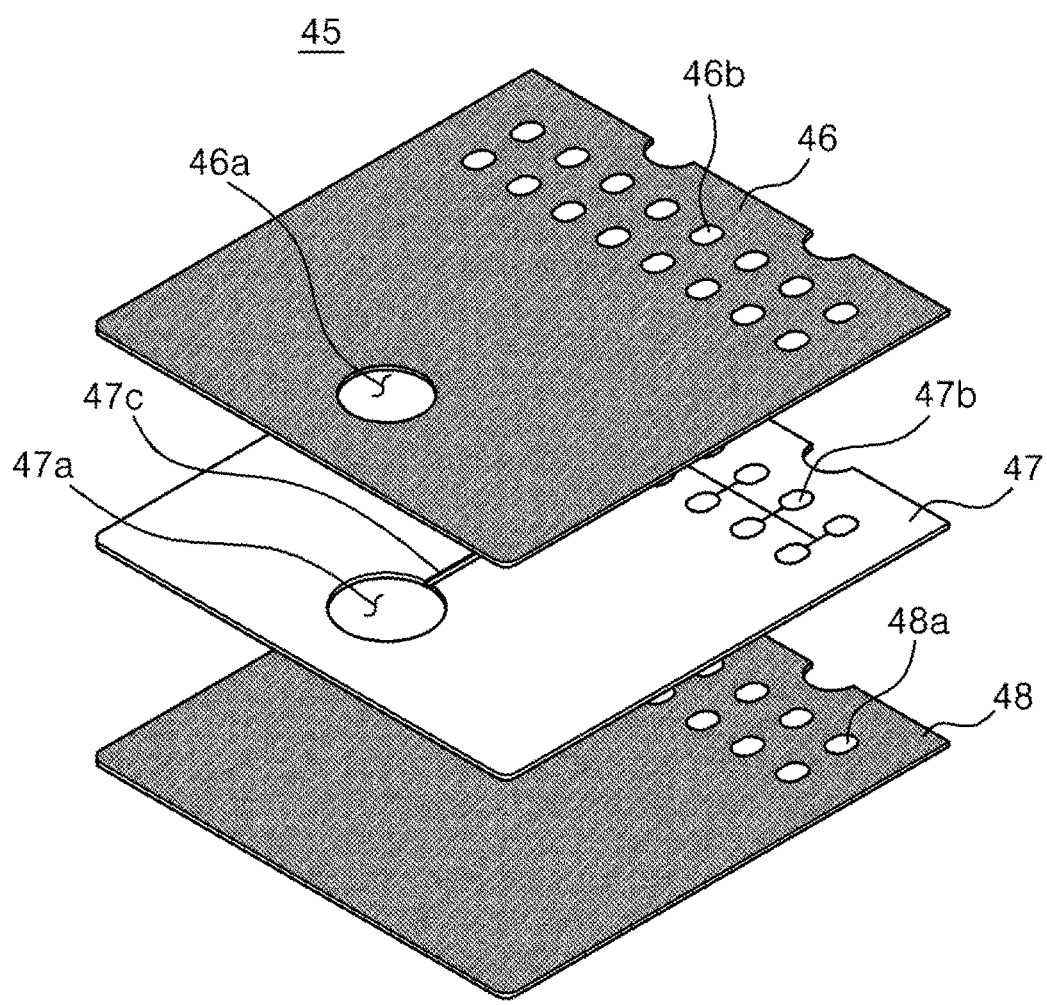
FIG. 5 is an exploded perspective view of a tester of the fluid test cartridge according to an embodiment.
Figure 6:
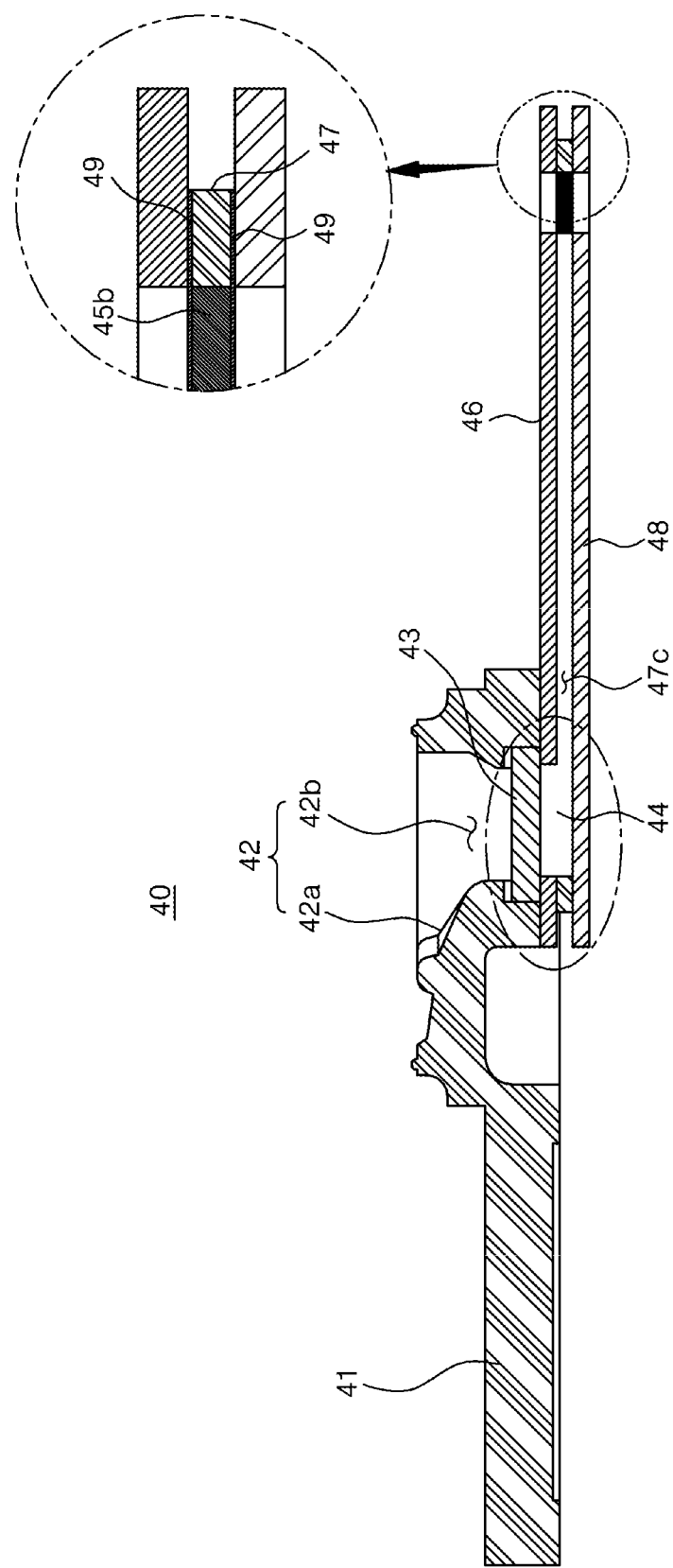
FIG. 6 is a cross-sectional view of the tester of the cartridge shown in FIG. 4, taken along line A-A'.
Figure 7:
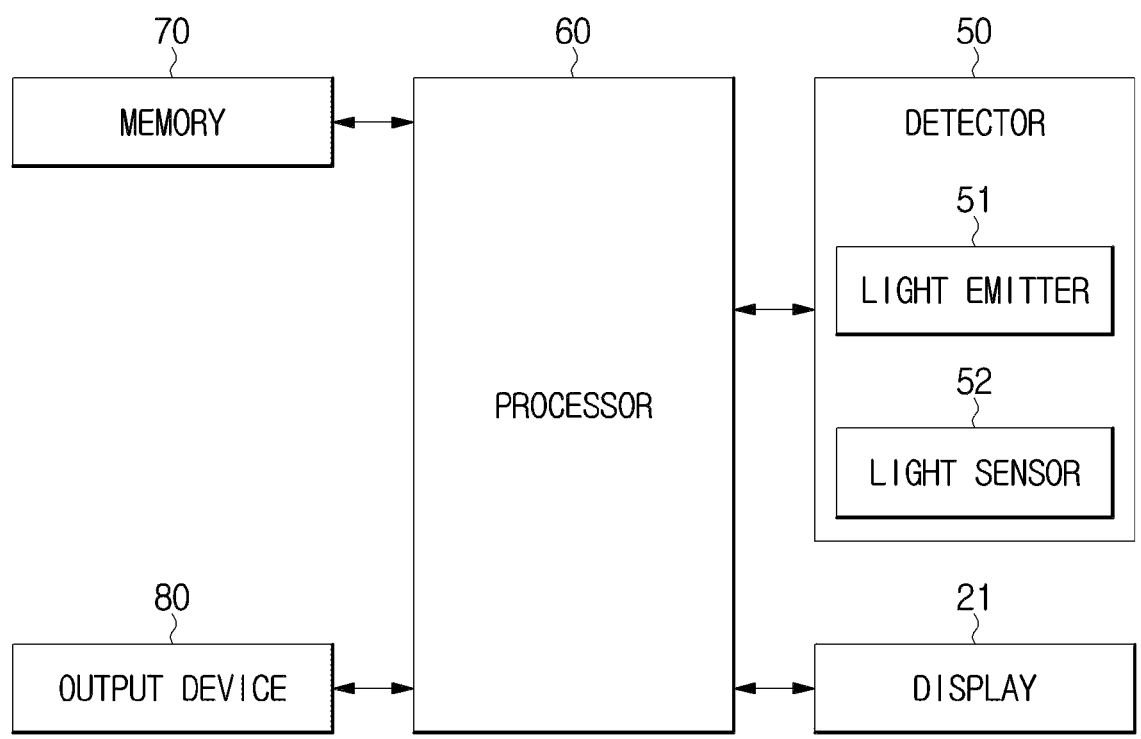
FIG. 7 is a control block diagram of a fluid test apparatus according to an embodiment.

FIG. 1 shows a fluid test apparatus to which a fluid test cartridge is coupled, according to an embodiment, FIG. 2 is an exploded perspective view of the fluid test cartridge according to an embodiment and a mounting member of the fluid test apparatus to which the fluid test cartridge is coupled, FIG. 3 shows a state in which the fluid test cartridge according to an embodiment is coupled to the mounting member of the fluid test apparatus, and FIG. 4 shows the fluid test cartridge according to an embodiment. FIG. 5 is an exploded perspective view of a tester of the fluid test cartridge according to an embodiment. FIG. 6 is a cross-sectional view of the tester of the fluid test cartridge shown in FIG. 4, taken along line A-A', and FIG. 7 is a control block diagram of a fluid test apparatus according to an embodiment. The following description refers to FIGS. 1 to 7 collectively in order to avoid redundant descriptions.

As shown in FIG. 1, according to an embodiment, a fluid test apparatus 1 to which a fluid test cartridge 40 is coupled may include a housing 10 forming an outer appearance and a door module 20 disposed at a front portion of the housing 10.

The door module 20 may include a display 21, a door 22, and a door frame 23. The display 21 and the door 22 may be disposed at a front portion of the door frame 23. In FIG. 1, the display 21 is located at an upper portion of the door 22, however, the display 21 may be located at any position (such as the bottom portion of the door) as long as it can effectively display information to a user.

The door 22 may be slidable. After the door 22 slides to open, the door 22 may be disposed behind the display 21.

The display 21 may display various analysis information about a fluid sample 111, such as a concentration of a first material in the fluid sample 111. The display 21 may be implemented as a touchscreen display such that the display 21 may receive various information, commands, etc. from a user's touch inputs.

The door frame 23 may include a mounting member 32 on which the fluid test cartridge 40 accommodating various reagents is mounted. The user may push up the door 22 to expose the area around the mounting member 32, mount the fluid test cartridge 40 on the mounting member 32, then push down the door 22 to close the area around the mounting member 32, and perform an analysis operation.

The fluid sample 111 may be injected into the fluid test cartridge 40, and may react with a reagent in a tester 45. When the fluid test cartridge 40 is inserted into the mounting member 32 and a pressing member 31 presses the fluid test cartridge 40, the fluid sample 111 injected into the fluid test cartridge 40 may be introduced into the tester 45.

In addition, the fluid test apparatus 1 may further include an output device 11 for outputting analysis results as a printout separately from the display 21. The output device may be a printer for printing the analysis results on a recording medium such paper or an adhesive label. Thus, the user may output test results through the output device 11, in addition to visually checking the test results through the display 21.

Referring to FIGS. 2 to 4, the fluid test cartridge 40 may be inserted into the mounting member 32 of the fluid test apparatus 1. The mounting member 32 may include a resting portion 32c on which the fluid test cartridge 40 is rested/disposed, and a pair of supports 32f for supporting the mounting member 32 in the fluid test apparatus 1 and connecting the mounting member to the housing 10.

The supports 32f may extend from both ends of a body 32e of the mounting member 32, and the resting portion 32c may be disposed at the center of the body 32e. A slit 32d may be formed adjacent to the resting portion 32c to prevent the tester 45 from generating errors when measuring test results of the fluid sample 111.

The mounting member 32 may have a plurality of contact portions 32a and 32b that contact the fluid test cartridge 40. In FIG. 2, the contact portions are shown as having a semicircular shape. However, the contact portions could also have a variety of other shapes, such as a rectangular shape, a triangular shape, or a snap fit connection shape such as a column with a thick distal protrusion. The tester 45 of the fluid test cartridge 40 may include a plurality of recesses 45a having shapes corresponding to the contact portions 32a and 32b. Thus, the recesses 45a may contact the contact portions 32a and 32b and form a close fit around the contacts portions. In the current embodiment, two recesses 45a may be provided to correspond to two contact portions 32a and 32b, but embodiments are not limited thereto and there may be one recess and one contact portion, or three or more recesses and contact portions.

The fluid test cartridge 40 may include a housing 41 forming an outer appearance of the fluid test cartridge 40, and the tester 45 in which the fluid sample 111 reacts with a reagent.

The housing 41 may support the fluid test cartridge 40 and have a shape that permits the user to manually grip the fluid test cartridge 40. According to an embodiment, as shown in FIGS. 2 and 3, a portion that is gripped by the user may be in the shape of a streamlined protrusion. Thus, the user may stably grip the fluid test cartridge 40. However, the housing 41 is not limited to the shape shown in FIGS. 2 and 3, and may also have any other shape.

Also, the fluid test cartridge 40 may have a sample feeder 42 for receiving fluid samples. The sample feeder 42 may include a feeding hole 42b through which the fluid sample 111 is introduced into the tester 45 and a sample feeding well 42a for directing feeding of the fluid sample 111.

The fluid sample 111 that is to be tested by the fluid test apparatus 1 may be directed into the sample feeder 42. Examples of the fluid sample 111 may include biological samples (for example, body fluids including blood, tissue fluids, and lymph fluids, saliva, and urine) or environmental samples for water-purity control or soil management, although the fluid test apparatus 1 could also receive and process other types of fluid samples. The fluid sample 111 may or may not be diluted. The fluid sample 111 may include a first material 110 which is a target material. The first material 110 may include at least one material selected from the group including of antibodies, DNA, RNA, oligosaccharide, peptide, small molecules, and proteins.

Referring to FIG. 2, the feeding hole 42b may be in the shape of a circle. However, the shape of the feeding hole 42b is not limited thereto, and the feeding hole 42b may be in the shape of a polygon or any other suitable shape. The user may drop the fluid sample 111 into the sample feeder 42 using a tool such as a pipette.

The sample feeding well 42a may be formed around the feeding hole 42b to be inclined downward toward the feeding hole 42b so as to cause the fluid sample 111 dropped around the feeding hole 42b to flow downwardly into the feeding hole 42b. More specifically, when the user fails to accurately drop the fluid sample 111 exactly into the feeding hole 42b, so that some of the fluid sample 111 falls adjacent the feeding hole 42b, the fluid sample 111 that has fallen around the feeding hole 42b may flow into the feeding hole 42b via the inclined surface of the sample feeding well 42a.

Also, the sample feeding well 42a may prevent contamination of the fluid test cartridge 40 due to the fluid sample 111 falling at an incorrect location, in addition to directing the supply of the fluid sample 111. That is, when the fluid sample 111 fails to fall into the feeding hole 42b, the sample feeding well 42a formed around the feeding hole 42b may prevent the fluid sample 111 from flowing onto the tester 45 or the portion gripped by the user. Accordingly, the sample feeding well 42a may prevent contamination of the fluid test cartridge 40 due to the fluid sample 111, while also preventing the user from contacting the fluid sample 111 which may be harmful to the human body.

In the current embodiment, the sample feeder 42 includes a single feeding hole 42b as shown in the drawings, however, the sample feeder 42 may include a plurality of feeding holes. When a plurality of feeding holes is provided, a plurality of different fluid samples may be simultaneously tested in one fluid test cartridge. Herein, the plurality of different fluid samples may be of a single type of sample obtained from different sources, different types of samples obtained from a single source, or the same type of sample in different states obtained from the single source.

As described above, since the housing 41 has a shape suitable to perform specific functions and may contact the fluid sample 111, the housing 41 may be made of a chemically and biologically inactive material that can be easily molded.

For example, the housing 41 may be formed of various materials, for example, acryl such as polymethylmethacrylate (PMMA), polysiloxane such as polydimethylsiloxane (PDMS), polycarbonate (PC), polyethylene such as linear low density polyethylene (LLDPE), low density polyethylene (LDPE), medium density polyethylene (MDPE), and high density polyethylene (HDPE), plastic materials such as polyvinyl alcohol, very low density polyethylene (VLDPE), polypropylene (PP), acrylonitrile butadiene styrene (ABS), and cycloolefin copolymer (COC), glass, mica, silica, and a semiconductor wafer.

However, these materials are examples of materials that can be used to form the housing 41, and materials used to form the housing 41 are not necessarily limited to these materials. The housing 41 according to an embodiment may also be formed using any chemically and biologically stable material with good mechanical processability.

Meanwhile, the tester 45 may be coupled or bonded to the fluid test cartridge 40. The fluid sample 111 injected through the sample feeder 42 may be introduced into the tester 45 and react with drying reagents 103 (see FIG. 8) to thereby be tested. As shown in at least FIGS. 4 and 5, the tester 45 may include a plurality of chambers 45b, and the drying reagents 103 may be contained in the chambers 45b to react with the first material 110 of the fluid sample 111. According to an embodiment, the drying reagents 103 may be used in the chamber 45b. This will be described later.

In this regard, the plurality of chambers 45b may accommodate various kinds of reagents. For example, the chambers 45b may contain a reagent for detecting a concentration of the first material 110 in the fluid sample 111. For example, the reagent may include a coloring agent showing different optical properties depending on the concentration of the first material 110 in the fluid sample 111. The fluid test apparatus 1 may detect optical properties through the light sensor 52, and calculate a concentration of the first material 110 based on the results of the detection with the processor 60.

The first material 110 which will be described below may be a target material included in the fluid sample 111 to be analyzed. For example, the first material 110 may be at least one material selected from the group including antibodies, DNA, RNA, an oligosaccharide, peptide, small molecules, and protein. Hereinafter, the structure of the tester 45 of the fluid test cartridge 40 will be described in more detail.

Referring to FIG. 5, the tester 45 of the fluid test cartridge 40 according to an embodiment may have a structure in which three plates, i.e., an upper plate 46, a middle plate 47, and a lower plate 48, are joined together. The upper plate 46 and the lower plate 48 may be coated with a light blocking ink to protect the fluid sample 111 moving to the chamber 45b from external light or to prevent errors while measuring optical properties in the chamber 45b. Each of the upper plate 46 and the lower plate 48 may have a thickness of 10 μm to 300 μm. The middle plate 47 may have a thickness of 50 μm to 300 μm. However, these thicknesses are merely exemplary.

A film used to form the upper plate 46 and the lower plate 48 of the tester 45 may be selected from among polyethylene films, such as a very low density polyethylene (VLDPE) film, a linear low density polyethylene (LLDPE) film, a low density polyethylene (LDPE) film, a medium density polyethylene (MDPE) film, and a high density polyethylene (HDPE) film, a polypropylene (PP) film, a polyvinyl chloride (PVC) film, a polyvinyl alcohol (PVA) film, a polystyrene (PS) film, and a polyethylene terephthalate (PET) film. However, these films are only examples, and any other chemically and biologically inactive films with good mechanical processability may also be used to form the upper plate 46 and the lower plate 48 of the tester 45.

The middle plate 47 of the tester 45 may be a porous sheet, unlike the upper plate 46 and the lower plate 48. The porous sheet used as the middle plate 47 may include at least one of cellulose acetate, Nylon 6.6, Nylon 6.10, and polyether sulfone. Due to its porous structure, the middle plate 47 may permit fluid to propagate therethrough, and thus the fluid sample 111 may move in the tester 45 without using a separate driving source such as a pump. Also, when the fluid sample 111 is hydrophilic, the middle plate 47 may be coated with a hydrophobic solution to prevent the fluid sample 111 from permeating into the interior of the middle plate 47.

The upper plate 46 may have an inlet 46a through which the fluid sample is introduced, and a region 46b corresponding to the chamber 45b may be processed to be transparent. For example, the region 46b may be transparent to visible light, ultraviolet light, or infrared radiation. Also, a region 48a of the lower plate 48 corresponding to the chamber 45b may be processed to be transparent. For example, the region 48a may be transparent to visible light, ultraviolet light, or infrared radiation. This processing may be performed to measure absorbance as an example of optical properties obtained by reactions taking place in the chamber 45b. Herein, absorbance is also called optical density, however, in the following description, the term "absorbance" will be used for convenience of explanation.

The middle plate 47 may also include an inlet 47a through which the fluid sample 111 is introduced, and the inlet 46a of the upper plate 46 may overlap with the inlet 47a of the middle plate 47 to form an inlet 44 of the tester 45. Also, the middle plate 47 may have a flow path channel 47c connecting the inlet 47a with a test portion 47b.

In the tester 45, various reactions for analysis of the fluid sample 111 may take place. When blood is used as the fluid sample 111, a reagent, which reacts with a specific component (particularly, plasma) of blood to express a color or change the color, may be accommodated in the chamber 45b, and then a color expressed in the chamber 45b may be optically detected and digitally converted to a numeric value. Based on the numeric value of the detected color, the presence/absence of the specific component in the blood, a proportion of the specific component, and/or a concentration of the specific component, etc. may be determined.

The fluid test cartridge 40 may be formed in such a manner that the tester 45 is bonded to the lower portion of the housing 41. More specifically, the tester 45 may be bonded to the lower side of the sample feeder 42 where the feeding hole 42b is provided.

The tester 45 may be adhered to the housing 41 using a pressure sensitive adhesive (PSA). The pressure sensitive adhesive may be adhered to an adherent within a short period of time at room temperature by low pressure of about finger pressure. When the pressure sensitive adhesive is peeled, cohesive failure is not caused and no residues remain on the surface of the adherent. However, the tester 45 may be bonded to the housing 41 by a double-sided adhesive, instead of the pressure sensitive adhesive. As another example, the tester 45 may be coupled with the housing 41 by inserting a protrusion into a groove. The protrusion and the groove may form a locking connection by way of a snap fit mechanism with an enlarged protrusion, or a dovetail connection.

The fluid sample 111 introduced through the feeding hole 42b may pass through a filter 43 to enter the tester 45 (FIG. 6). The filter 43 may be inserted into the feeding hole 42b of the housing 41.

The filter 43 may include at least one porous membrane having a plurality of pores to filter out materials having a predetermined size or greater that are included in the fluid sample 111. For example, the filter 43 may include two layers of filters. According to an embodiment, a first filter may be formed of a glass fiber, an unwoven fabric, an absorbent filter, or the like, and a second filter may be formed of polycarbonate (PC), polyether sulfone (PES), polyethylene (PE), polysulfone (PS), or polyacrylsulfone (PASF). The filter 43 could also include a single layer, or three or more layers in some embodiments.

When the filter 43 has a double-layered structure as described above, the fluid sample 111 having passed through an upper filter may be filtered once more by a lower filter. Also, the double-layered structure may prevent the filter 43 from being torn or damaged when a large amount of particles greater than the pore size of the filter 43 are simultaneously introduced. However, the embodiment is not limited thereto, and the filter 43 may include three or more layers. In this case, a function of filtering the fluid sample 111 may be further enhanced, and stability of the filter 43 may also be further improved. Each filter 43 may be processed using an adhesive material (not shown) such as a double-sided adhesive.

The tester 45 may include the inlet 44 through which the fluid sample 111 passed from the filter 43 is introduced, the flow path channel 47c through which the introduced fluid sample 111 moves, and the chamber 45b in which the fluid sample 111 reacts with a reagent. A concentration of the first material 110 may be detected using a difference in optical sensitivity between the second chamber and the first chamber. Herein, absorbance, a degree of luminescence, and fluorescence sensitivity may be used as an optical sensitivity. The optical sensitivity may also be referred to as an "optical measurement value."

Meanwhile, the upper plate 46, the middle plate 47, and the lower plate 48 may be bonded by double-sided adhesive tapes 49. More specifically, the upper plate 46, the middle plate 47, and the lower plate 48 may be bonded by applying the double-sided adhesive tapes 49 to both an upper surface and a lower surface of the middle plate 47.

The plurality of chambers 45b of the fluid test cartridge 40 may be isolated from each other. For example, the chambers 45b may include a first chamber, a second chamber, and a third chamber, but the number of the chambers 45b is not limited thereto. According to an embodiment of the disclosure, a drying reagent 103 including a second material 102 may be contained in the chamber 45b. The first material 110 in the fluid sample 111 may react with the second material 102 in the drying reagent 103 to coagulate. In order to quantitatively calculate an agglutination reaction, the detector 50 (FIG. 7) may measure an optical sensitivity in the chamber 45b to measure a concentration of the first material 110. According to another embodiment of the disclosure, a first drying reagent may be accommodated in the first chamber, and a second drying reagent may be accommodated in the second chamber. The first drying reagent may be suitable to measure a low concentration of the first material, and the second drying reagent may be suitable to measure a high concentration of the first material. As such, by containing different reagents in different chambers, it may be possible to measure two or more kinds of reactivity of a fluid sample. This will be described later.

FIG. 7 is a control block diagram of a fluid test apparatus according to an embodiment.

As shown in FIG. 7, the fluid test apparatus 1 may include a detector 50 for detecting an optical sensitivity caused by a reaction between the second material 102 in the drying reagent 103 accommodated in the chamber 45b and the first material 110 in the fluid sample 111, memory 70 in which control data and programs required for controlling overall operations of the fluid test apparatus 1 are stored, a processor 60 for controlling overall operations of the fluid test apparatus 1, an output device 80 for outputting analysis results of the fluid sample 111, and a display 21 for visually displaying various information. Although not shown in FIG. 7, the apparatus may also include communication circuitry configured to communicate with an external electronic device via a wired or wireless connection. For example the apparatus could include a wireless Wi-Fi, LTE, NFC, or Bluetooth communication chip, or a wired connection such as a USB port. The output device 80 and the display 21 have been described above in detail, and accordingly, the other components will be described below.

The detector 50 may detect an optical sensitivity, and the processor 60 may calculate various analysis values used for diagnosis of a target object, such as a concentration value of the first material 110, based on detection results. The processor is an electronic hardware chip and may also be referred to as a microcontroller, controller, or control unit.

The detector 50 may include a light emitter 51 for emitting light and a light sensor 52 for receiving and sensing light. The light emitter 51 may be at least one element selected from the group including a white light emitting diode (LED), an ultraviolet LED, a blue LED, a green LED, a yellow LED, a red LED, and an infrared LED. That is, the light emitter 51 may be implemented as various known types of sensors and devices that emit light, although there is no particular restriction on the type of light source that may be used.

The light sensor 52 may concentrate or detect light on the chamber 45b. For example, the light sensor 52 may be implemented through a photodiode or the like that detects light on the chamber 45b and converts the light into electric energy. The light sensor 52 could also be a camera or an optical sensor that can detect visible, ultraviolet, or infrared radiation and convert the detected electromagnetic radiation into electrical signals for the processor 60 to process.

The light emitter 51 and the light sensor 52 may be disposed to face each other with the chamber 45b in between. Accordingly, the light sensor 52 may detect optical properties according to a reaction between the drying reagent 103 and the fluid sample 111 in the chamber 45b. For example, according to an embodiment, the drying reagent 103 may be pre-filled in the chamber 45b. The drying reagent 103 may be applied on one side of the chamber 45b in a dried solid state. The light emitter 51 may be disposed adjacent to a region 46n provided in the upper plate 46 to emit light to the chamber 45b. Correspondingly, the light sensor 52 may be disposed adjacent to a region 48a provided in the lower plate 48 to detect or concentrate light on the chamber 45b.

When the light sensor 52 is implemented as a photodiode, a magnitude of electric energy output from the light sensor 52 may depend on the concentration of the first material 110. The processor 60 may calculate an optical sensitivity of the first material 110 based on the electric energy output from the light sensor 52.

The fluid test apparatus 1 may include a memory 70. The memory 70 could be a volatile memory, or a non-volatile memory.

The memory 70 may be implemented through at least one type of storage medium among a flash memory type, a hard disk type, a multimedia card micro type, a card type memory (e.g., SD or XD memory), random access memory (RAM), static random access memory (SRAM), read only memory (ROM), electrically erasable programmable read-only memory (EEPROM), programmable read-only memory (PROM), magnetic memory, magnetic disk, and an optical disk. However, the disclosure is not limited thereto, and the memory 70 may be implemented in other forms.

The memory 70 may store control data and a control program used to control overall operations of the fluid test apparatus 1. Accordingly, the processor 60 may control overall operations of the fluid test apparatus 1 using the data stored in the memory 70 and/or the control program.

A software program that is executable by the processor 60 for performing a method of correcting the optical signal value of the first material 110 may be stored in the memory 70. The memory 70 may store data about the characteristic information of the drying reagent 103.

The memory 70 may also store data related to a user interface. Herein, the user interface is a display screen configured to allow a user to easily input various setting commands, control commands, etc. for the fluid test apparatus 1, to easily control programs stored in the memory 70, and to easily understand various information such as results of analysis produced by the fluid test apparatus 1. For example, the user interface may be a graphical user interface that graphically implements a screen displayed on the display 21 to conveniently display various information and relay commands from the user to the fluid test apparatus 1, or relay instructions from the fluid test apparatus 1 to the user. A method of providing various information through the user interface, a method of displaying and arranging icons for receiving various setting commands and control commands, etc. may be implemented as an algorithm or a program and stored in the memory 70. Accordingly, the processor 60 may create a user interface using data stored in the memory 70, and display the user interface on the display 21. Alternatively, the algorithms, programs, etc., as described above, may be stored in an external storage device. Accordingly, the processor 60 may receive data for the user interface derived by an external device through an algorithm and a program through a communication network, and may display the data on the display 21.

On the other hand, the data stored in the memory 70 may be updated. For example, the user interface stored in the memory 70, a method of correcting an optical signal value of the first material 110, data about characteristics information of the drying reagent 103, etc. may be updated through a wired communication network or a wireless communication network, via the communication circuitry. At this time, the data stored in the memory 70 may be updated according to a control command from the user, or automatically at regular intervals.

The memory 70 and the processor 60 may be implemented separately or may be integrated into a system on chip (SOC) built in the fluid test apparatus 1.

The fluid test apparatus 1 may be provided with the processor 60. The processor 60 may be implemented by a device such as a hardware processor or integrated circuit capable of performing various arithmetic operations. The processor 60 may control overall operations of components included in the fluid test apparatus 1 through control signals.

For example, when a command for outputting analysis results is received from the user, the processor 60 may send a control signal to the output device 80 for the output device 80 to output the analysis results. As another example, the processor 60 may send a control signal to the display 21 for controlling the display 21 to display the analysis results for the fluid sample 111.

The processor 60 may analyze the first material 110 in the fluid sample 111 using the optical properties of the fluid sample 111 that are detected through the detector 50.

The processor 60 may determine a concentration value of the first material 110 which is a target material, based on the optical sensitivity. That is, the processor 60 may determine a concentration value of the first material 110 based on absorbance, luminescence, or fluorescence sensitivity. For example, as a concentration of the first material 110 increases according to the drying reagent 103, the optical sensitivity may be increased or decreased. The processor 60 may derive a concentration value of the first material 110 from the optical sensitivity on the chamber 45b using data stored in the memory 70.

The processor 60 may display the user interface on the display 21. Herein, the user interface is a display screen configured to enable a user to more easily control components and programs of the fluid test apparatus 1 and to easily understand various information. The user interface may be a graphical user interface that graphically implements a screen displayed on the display 21 to conveniently display information, and relay commands between the user and the fluid test apparatus 1.

For example, the graphical user interface may be implemented to display icons, buttons, etc. for easily receiving various control commands from the user in an area on a screen displayed through the display 21, and to display various information through at least one widget, a pop-up message, etc. in another area on the screen. The graphical user interface may also display a variety of graphs, charts, or other measured data that is detected by the detector 50 and processed by the processor 60. For example, the graphical user interface could display a concentration value of the first material 110, and/or absorbance, luminescence, or fluorescence sensitivity values.

Figure 8:
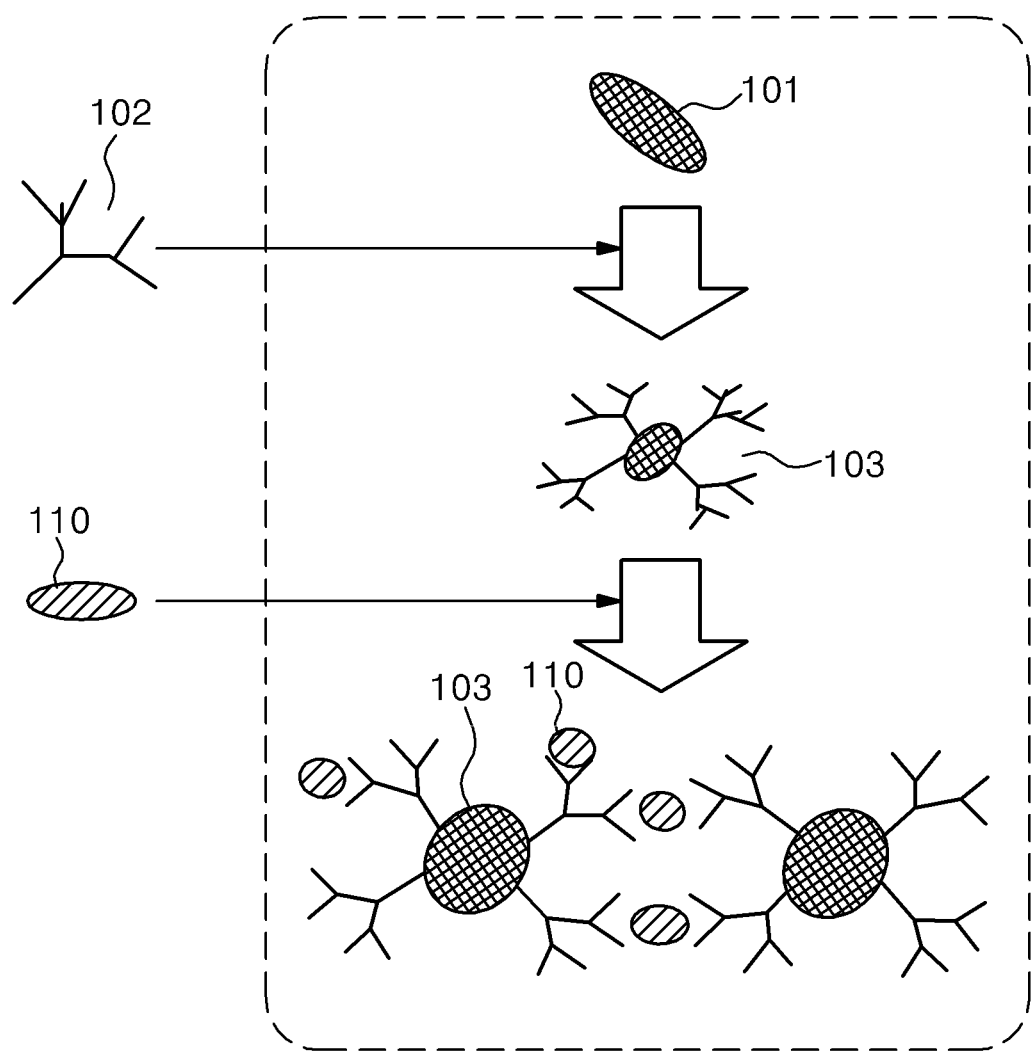
FIG. 8 is a schematic view for describing a process in which a fluid sample reacts with a drying reagent, according to an embodiment.

FIG. 8 is a schematic view for describing a process in which a fluid sample reacts with a drying reagent, according to an embodiment.

As shown in FIG. 8, the drying reagent 103 may include a non-metallic particle 101 and a second material 102 that is able to specifically bind to the first material 110 which is a target material.

When the second material 102 is bounded to the non-metallic particle 101 and the fluid sample 111 is introduced, the first material 110 and the second material 102 in the fluid sample 111 may be combined to cause an agglutination reaction.

The non-metallic particle 101 may be composed of at least one of a monomer and a complex. The non-metallic particle 101 may have optical properties. More specifically, the non-metallic particle 101 may have light absorbing or luminescent characteristics. The non-metallic particle 101 may have optical properties by applying a coloring material, such as a light absorbing material, a light emitting material or a fluorescent material, on the inside or on a surface of the non-metal particle 101.

Also, the non-metallic particle 101 may be a nano-sized particle. According to an embodiment, the diameter of the non-metallic particle 101 may be 1 nm or more. In some embodiments, the nano-sized particle may be less than 100 nm in diameter. The non-metallic particle 101 may be at least one material selected from the group including carbon nanoparticles, ceramic nanoparticles, and polymeric nanoparticles.

The ceramic nanoparticle may be at least one material selected from the group including glass and silica nanoparticles.

The polymeric nanoparticle may be at least one material selected from the group including polymethyl methacrylate, polystyrene, cellulose, latex, hydrogel, and agarose.

The first material 110 may be a target material in the fluid sample 111, and may be a material whose concentration is to be measured by the fluid test apparatus 1. The first material 110 may include at least one selected from the group including antigens, DNA, RNA, oligosaccharide, peptide, small molecules, and protein.

The second material 102 may be a material constituting the drying reagent 103. The second material 102 may be bound to the non-metallic particle 101 to constitute the drying reagent 103. The second material 102 may be a material that is specifically bound to the first material 110. The second material 102 may be at least one selected from the group including antibodies, oligonucleotides, and proteins.

For example, when the first material 110 is an antigen and the second material 102 is an antibody, the first material 110 and the second material 102 may be agglutinated because of the specific reaction between the antigen and the antibody. The detector 50 of the fluid test apparatus 1 may measure a degree of agglutination to determine a concentration of the first material 110.

Figure 9:
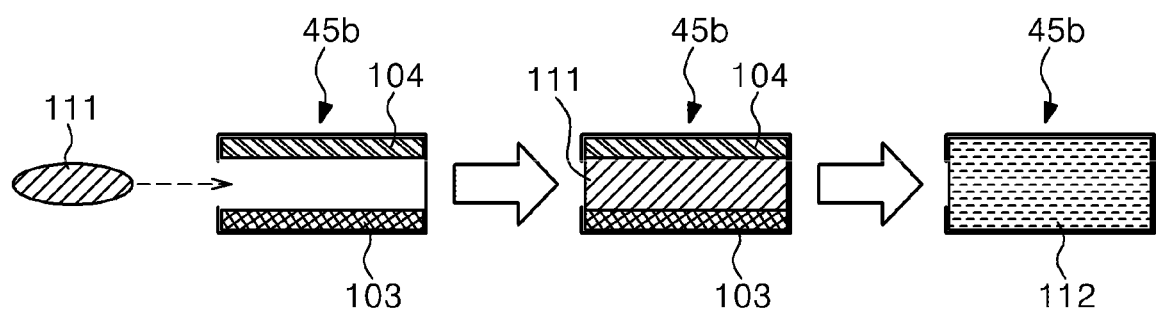
FIG. 9 is a view for schematically describing a process in which a fluid sample reacts with a drying reagent in a chamber, according to an embodiment.

FIG. 9 is a view for schematically describing a process in which a fluid sample reacts with a drying reagent in a chamber, according to an embodiment.

As shown in FIG. 9, the drying reagent 103 may be inserted onto at least one surface of the at least one chamber 45b. As shown in FIG. 9, the chamber 45b may include a first attachment surface at the upper portion and a second attachment surface at the lower portion, although it is not limited thereto. However, it may be also possible that the drying reagent 103 is applied to only one surface of the chamber 45b. That is, it may be possible that the drying reagent 103 is applied to both the first attachment surface and the second attachment surface of the chamber 45b or to any one of the first attachment surface and the second attachment surface of the chamber 45b.

The drying reagent 103 may be used to measure a concentration of the first material 110 in the fluid sample 111, and may be inserted into the chamber 45b in a dried solid state. As the fluid sample 111 is injected through the flow path channel 47c, the drying reagent 103 may come into contact with the fluid sample 111 and change to a liquid form, thereby being mixed with the fluid sample 111. Accordingly, only a mixed solution 112 may exist in the chamber 45b.

Reference numeral 104 shown in FIG. 9 denotes a chemical mixture containing a buffer for buffering a reaction between the fluid sample 111 and the drying reagent 103 in the chamber 45b.

At this time, the drying reagent 103 may include a buffer for the buffering effect and various materials for measuring the first material 110 which is a target material existing in the fluid sample 111.

The drying reagent 103 may contain a buffering agent and a stabilizer for the buffering effect. The stabilizer may be used to prevent degradation of protein when drying is carried out to produce the drying reagent 103. Examples of the stabilizer include sucrose, trehalose, D-sorbitol, and the like.

In addition, the drying reagent 103 may include a plasticizer, a vinyl, and a polymeric chemical for the processability of the drying reagent 103. The materials may be used to facilitate insertion of the drying reagent 103 into the chamber 45b.

In addition, the drying reagent 103 may contain an activator. The activator may be added to increase the activity of agglutination reaction due to the specific binding of the first material 110 to the second material 102. As the activator, an enhancer, a surfactant, or the like may be used.

In addition, the drying reagent 103 may include a coloring agent showing different optical properties depending on a concentration of the first material 110 in the fluid sample 111.

In addition, the drying reagent 103 may include a material for maintaining an appropriate pH level in order to more accurately detect the optical properties of the fluid sample 111. When the pH of the fluid sample 111 is out of a specific range (i.e., too acidic or too basic), it may be difficult to measure an optical sensitivity, and accordingly, the drying reagent 103 may include a material for buffering/adjusting the pH of the fluid sample 111.

Also, the drying reagent 103 may contain an internal standard material. The internal standard material may include a first material which is produced by being dissolved through mixing with the fluid sample 111. For example, when sodium (Na), among materials existing in the fluid sample 111, is a first material that is a target material, sodium chloride (NaCl) may be selected as an internal standard material. When the fluid sample 111 enters the chamber 45b, the internal standard material may be mixed with the fluid sample 111 to change from a solid state to a liquid state to thus be dissolved into the ionic state of Na+ and Cl—. The internal standard material may be dissolved to change a concentration of the first material in the chamber 45b.

The same kind of drying reagent 103 or different kinds of drying reagent 103 may be accommodated in the respective chambers 45b. Accordingly, the user may select the fluid test cartridge 40 containing the drying reagent 103 related to the first material 110 to be measured, and mount the selected fluid test cartridge 40 on the door frame 23 to easily obtain a concentration of the first material 110.

On the other hand, concentrations of internal standard materials contained in the first drying reagent contained in the first chamber and the second drying reagent contained in the second chamber may be the same or different. For example, the first chamber may include a drying reagent containing no internal standard material, that is, a drying agent in which a concentration of the internal standard material is zero. Also, the second chamber may include a drying reagent containing an internal standard material of a preset concentration. A concentration, absorbance, luminescence, fluorescence, etc. of the first material to be measured may be the same or different for the individual chambers. Hereinafter, values that can be derived using the optical properties of the fluid sample, such as the concentration, absorbance, luminescence, and fluorescence of the first material, are collectively referred to as optical signal values of the first material.

According to an embodiment of the disclosure, a drying reagent suitable to measure a low concentration of a first material may be accommodated in the first chamber, and a drying reagent suitable to measure a high concentration of a first material may be accommodated in the second chamber. The drying reagent suitable to measure a low concentration of a first material may include antibodies that are not bound to a high concentration of a first material. Accordingly, it may be possible to increase the ability to detect a low concentration of a first material. In contrast, the drying reagent suitable to measure a low concentration of a first material may include antibodies that are not bound to a low concentration of a first material. Accordingly, it may be possible to increase the ability to detect a high concentration of a first material.

A concentration of the internal standard material injected into each chamber 45b may be preset. For example, drying reagents may have been set in advance for the individual chambers of the fluid test cartridge 40, and information about the drying reagents for the individual chambers may be mapped to identification information associated the fluid test cartridge 40. Herein, the identification information may be information for identifying the fluid test cartridge 40, such as a QR code, a bar code, etc., and characteristic information of the drying reagent 103 injected onto the chamber 45b may be mapped and stored. The identification may be attached to a portion of the fluid test cartridge. The characteristic information of the drying reagent 103 may include information about a degree in change of a concentration value of the first material 110 according to a degree in change of an optical signal value of the first material 110. In addition, the characteristic information of the drying reagent 103 may include information about a concentration of an injected internal standard material, a concentration of the first material 110 that is discharged as it reacts with the fluid sample 111, etc.

The processor 60 may determine differences in concentration of the first material 110 between the chambers 45b based on the identification information, and calculate a degree of change between optical signal values of the first material 110 between the chambers 45b from the results of detection through the detector 50. Accordingly, the processor 60 may determine a correction value for the concentration of the first material 110 by comparing the degrees of change of the optical signal values with density differences of the first material 110 mapped to the identification information.

As shown in FIG. 9, according to an embodiment of the disclosed disclosure, the drying reagent 103 is inserted into the chamber 45b, and the fluid sample 111 enters the chamber 45*b* through the flow path channel 47*c*, so that a reaction is carried out. Conventionally, a reagent and a fluid sample accommodated in different containers were transported to another container to carry out a reaction, so that there was high potential for contamination when the reagent and the fluid sample are transported. According to an embodiment of the disclosed disclosure, it may be possible to prevent such contamination from occurring, thereby preventing or at least reducing errors in test results.

FIGS. 10*a*-10*d* are graphs showing absorbances of a drying agent for the concentration of a fluid sample when non-metallic particles of the drying reagent are carbon nanoparticles.

More specifically, FIGS. 10*a*-10*d* are graphs of absorbances measured when a first material 110 reacts with a drying reagent obtained by bonding a second material to carbon nanoparticles and drying the resultant material. Herein, the second material 102 may be an antibody, more specifically, a C-reactive protein (CRP) antibody. Also, the first material 110 may be an antigen, more specifically, a C-reactive protein (CRP) antigen.

Figure 10A:
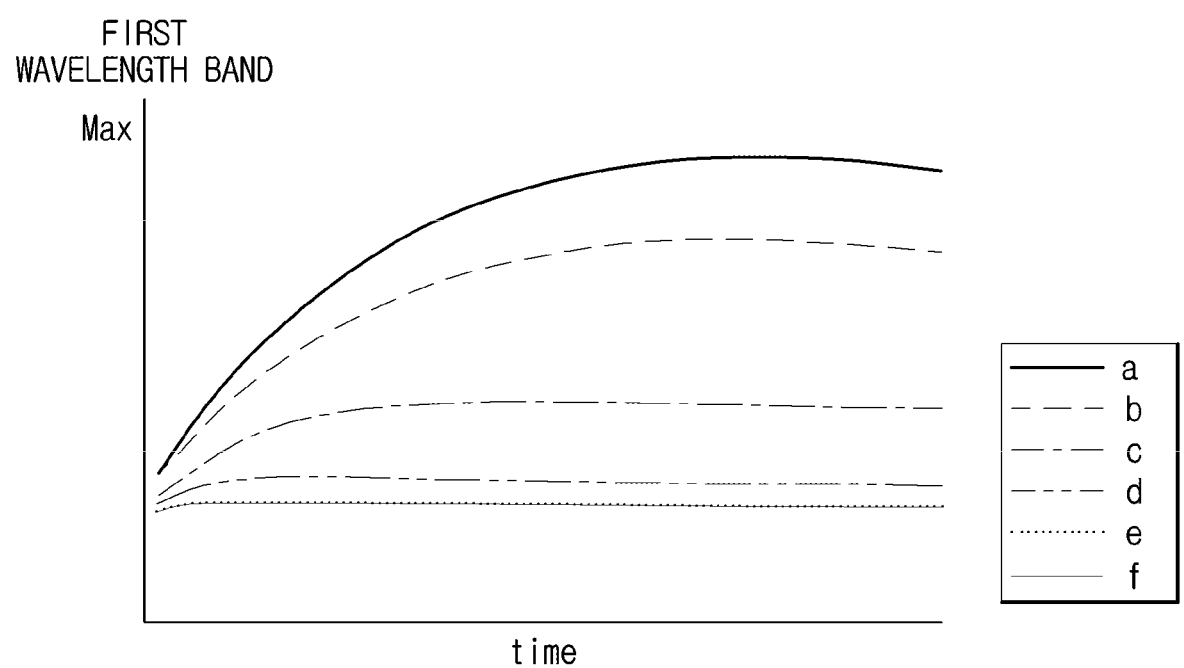
FIGS. 10a, 10b, 10c, and 10d are graphs showing absorbance of a drying agent for the concentration of a fluid sample when non-metallic particles of the drying reagent are nanoparticles.
Figure 10B:
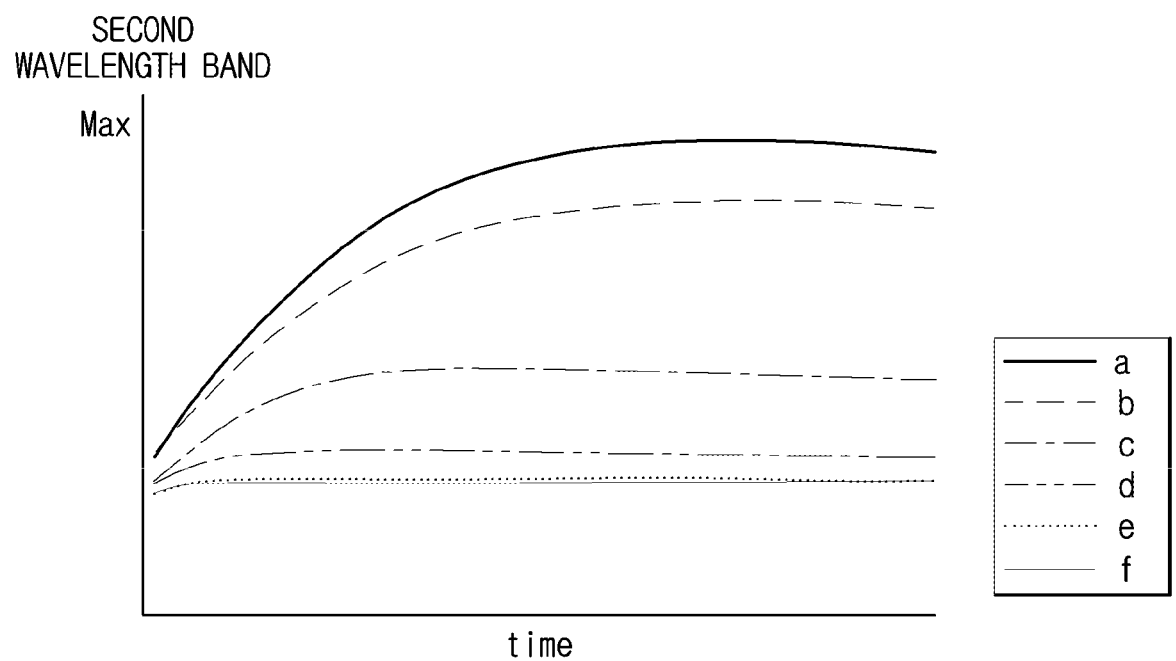
Figure 10C:
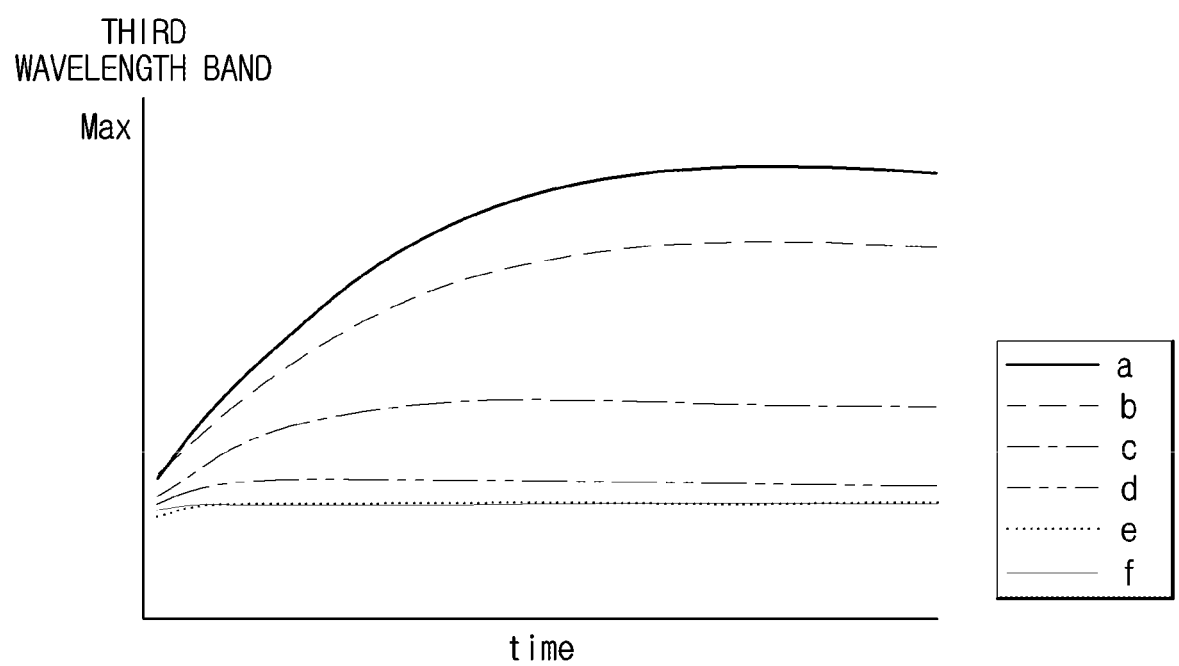
Figure 10D:
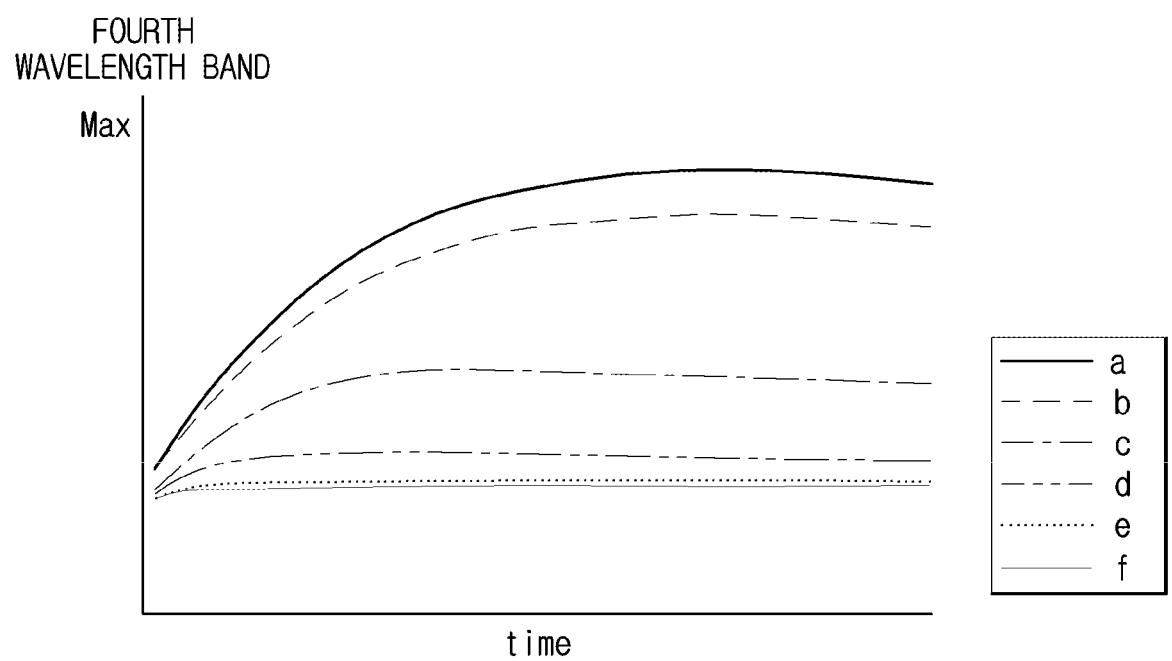

FIG. 10*a* is a graph showing absorbance of a first material according to the concentrations a, b, c, d, e, and f of the first material, measured in a first wavelength band, FIG. 10*b* is a graph showing absorbance of a first material according to the concentrations a, b, c, d, e, and f of the first material, measured in a second wavelength band, FIG. 10*c* is a graph showing absorbance of a first material according to the concentrations a, b, c, d, e, and f of the first material, measured in a third wavelength band, and FIG. 10*d* is a graph showing absorbance of a first material according to the concentrations a, b, c, d, e, and f of the first material, measured in a fourth wavelength band. According to an embodiment of the disclosure, the first to fourth wavelength bands may be at least a part of a region corresponding to 400 to 810 nm. Further, the first to fourth wavelength bands may overlap.

In FIGS. 10*a* to 10*d*, the x-axis represents time, and the y-axis represents absorbance. The maximum value on the y-axis may be 0.3 to 1.2.

As seen from FIGS. 10*a* to 10*d*, even when carbon nanoparticles are used as the non-metallic particles 101, absorbance may be distinctly measured according to the concentration of the first material throughout the entire wavelength.

Figure 11A:
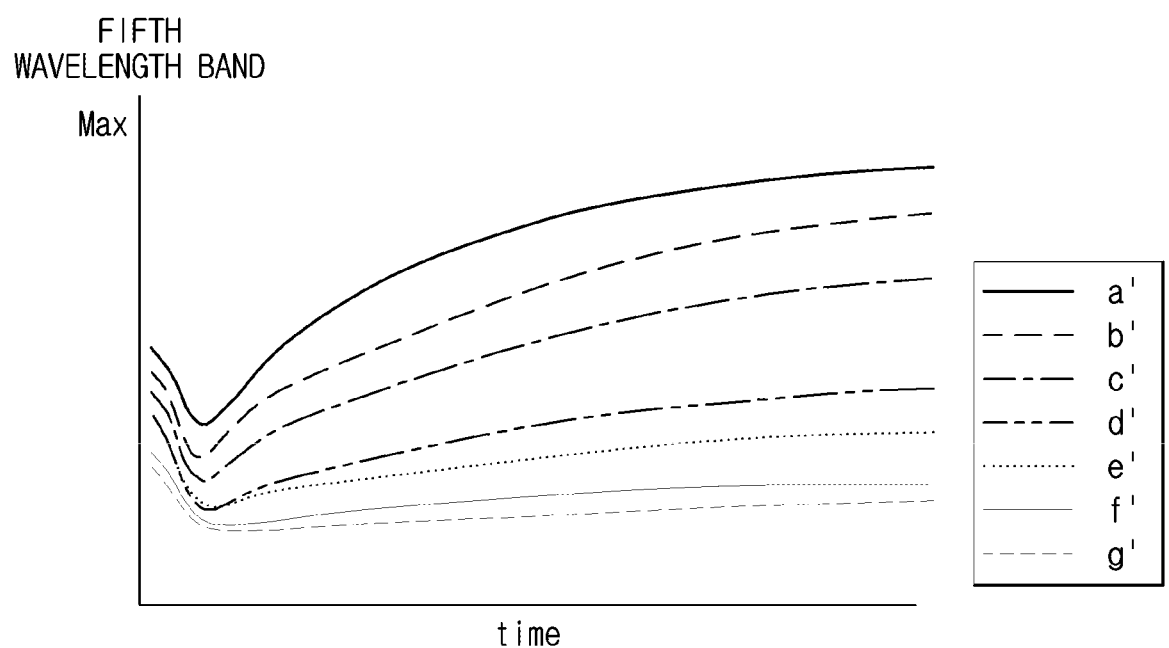
FIGS. 11a and 11b are graphs showing measured absorbance of a fluid sample according to the concentration of the fluid sample when non-metallic particles of a drying agent are cellulose.
Figure 11B:
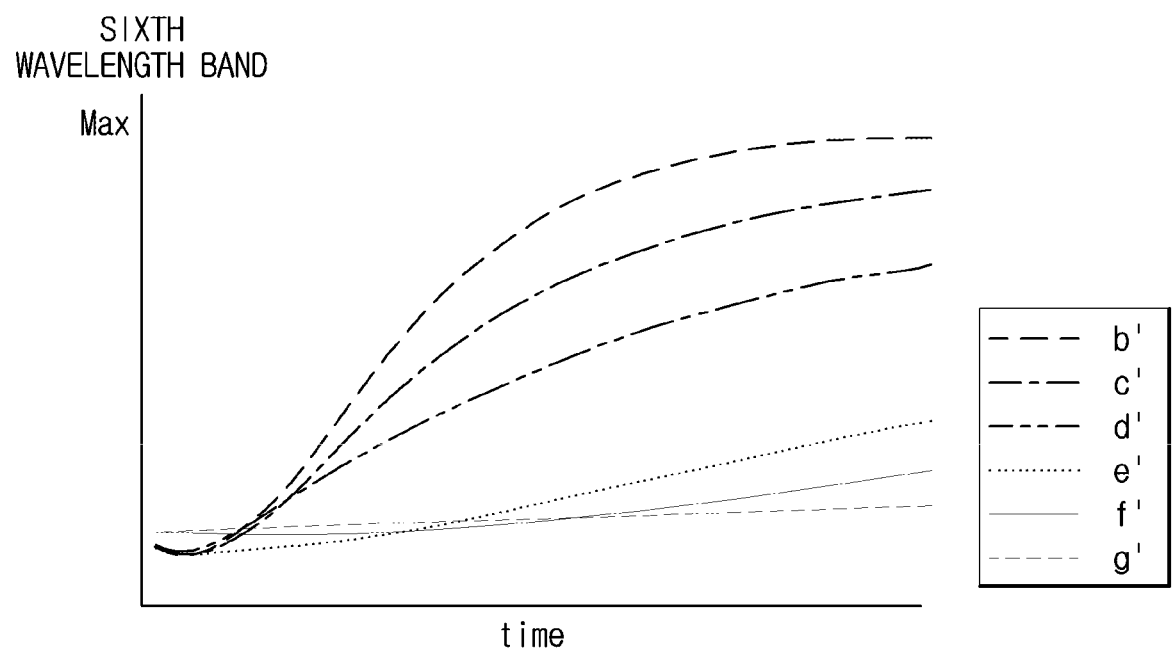
Figure 12A:
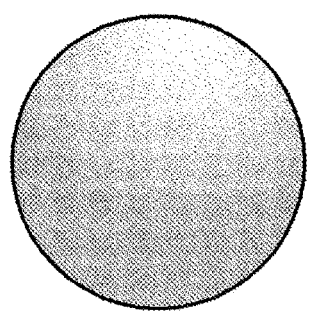
FIGS. 12a through 12e show various shapes of non-metallic particles according to an embodiment.
Figure 12B:
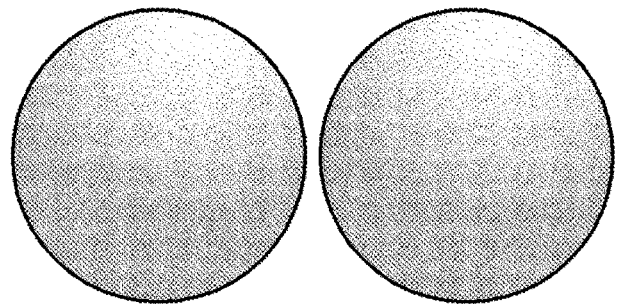
Figure 12C:
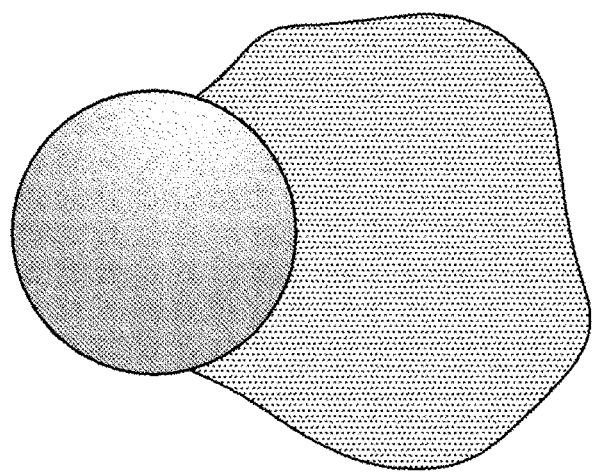
Figure 12D:
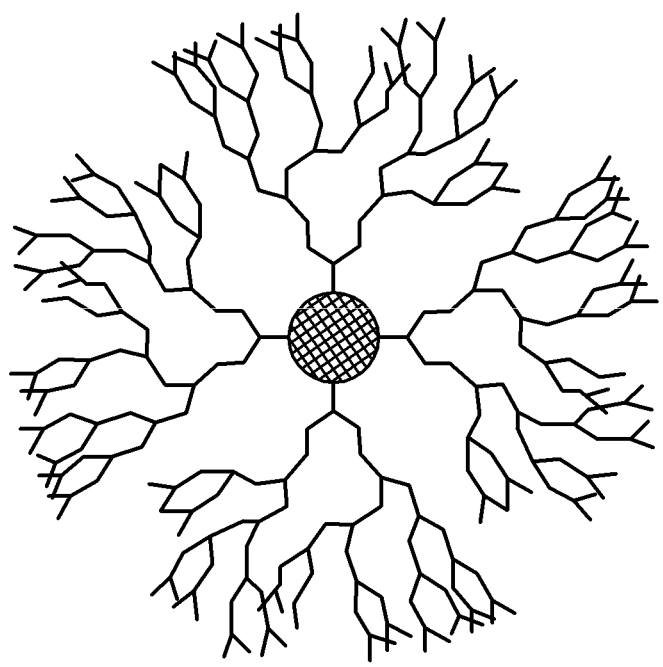
Figure 12E:
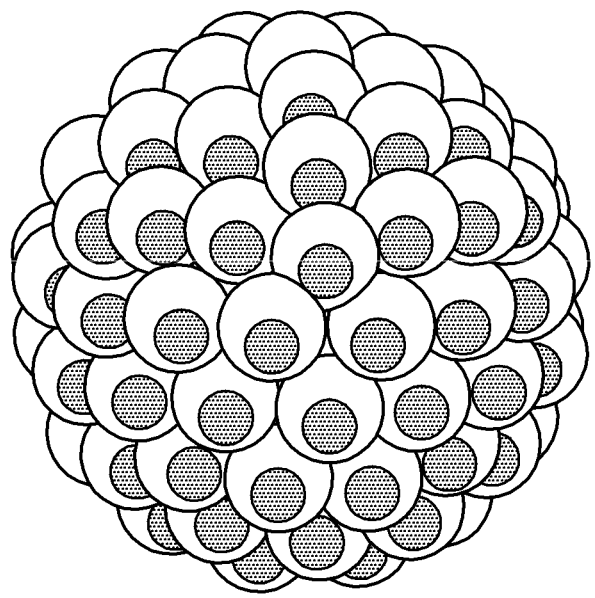

FIGS. 11*a* and 11*b* are graphs showing measured absorbances of a fluid sample according to the concentration of the fluid sample when non-metallic particles of a drying agent are cellulose.

More specifically, FIGS. 11*a* and 11*b* are graphs of absorbances measured when a first material reacts with a drying reagent obtained by bonding a second material to cellulose particles and then drying the resultant material. Herein, the second material 102 may be an antibody, more specifically, a C-reactive protein (CRP) antibody. The first material 110 is an antigen, more specifically, a C-reactive protein (CRP) antigen.

FIG. 11*a* is a graph showing absorbance of a first material according to the concentrations a', b', c', d', e', f', and g' of the first material, measured in a fifth wavelength band. FIG. 11*b* is a graph showing absorbance of the first material according to the concentrations b', c', d', e', f', and g' of the first material, measured in a sixth wavelength band. According to an embodiment of the disclosed disclosure, the fifth and sixth wavelength bands may be at least a part of a region corresponding to 400 to 810 nm. The fifth and sixth wavelength bands may overlap.

In FIGS. 11*a* and 11*b*, the x-axis represents time, and the y-axis represents absorbance. The maximum value on the y-axis may be from 5 to 9.

As seen from FIGS. 11*a* and 11*b*, even when cellulose particles are used as the non-metallic particles 101, absorbance may be distinctly measured according to the concentration of the first material throughout the entire wavelength.

As shown in FIGS. 10*a* to 10*d*, and 11*a* and 11*b*, when the drying reagent 103 includes non-metallic particles 101, various wavelengths may be selected to detect absorbance of the first material because the non-metallic particles 101 can absorb the entire wavelength of visible light. Conventionally, a wavelength width that can be selected was narrow. Accordingly, errors often occurred in test results when the wavelength changes. However, according to the embodiment of the disclosed disclosure, since non-metallic particles can absorb the entire wavelength of visible light, wavelength fluctuation may be less likely to affect test results.

FIGS. 12*a* to 12*e* shows various shapes of non-metallic particles according to various embodiments.

As shown in FIGS. 12*a* to 12*e*, non-metallic particles according to an embodiment of the disclosure may have various shapes. A non-metal particle 101*a* shown in FIG. 12*a* may be in the form of a single sphere. A non-metallic particle 101*b* shown in FIG. 12*b* may be in the shape of two spheres, and the two spheres may contact each other to be symmetrical with respect to each other and have a same size and a same shape. A non-metallic particle 101*c* shown in FIG. 12*c* may include two separate portions that contact each other but have different shapes. A non-metallic particle 101*d* in FIG. 12*d* may be in the shape of a dendrimer. The dendrimer represents a molecular form having a regular branch structure. A non-metallic particle 101*e* shown in FIG. 12*e* may be in the shape of a single large sphere composed a plurality of smaller individual spheres that are agglomerated. As described above, the non-metallic particles 101 may have various shapes, and are not limited to the shapes shown in FIGS. 12*a* to 12*e*. That is, the non-metallic particles 101 may be formed in the shape of a polygon, other than the shapes shown in FIG. 12, or may have non-uniform shapes.

FIG. 13 is a flowchart showing a method for controlling a fluid test apparatus according to an embodiment.

As shown in FIG. 13, the method for controlling the fluid test apparatus may include: operation S200 of mounting a fluid test cartridge on a housing; operation S210 in which a pressing member in the housing presses the fluid test cartridge to move a fluid sample in the fluid test cartridge to at least one chamber of the fluid test cartridge; operation S220 in which the fluid sample moved into the at least one chamber reacts with a drying reagent containing non-metallic particles bound to a second material that is specifically bound to a first material in the fluid sample in the at least one chamber; and operation S230 in which a detector measures the reaction in the fluid test cartridge through an optical sensitivity.

In the operation S230 in which the detector measures the reaction in the fluid test cartridge through the optical sensitivity, a light emitting portion may irradiate light to the fluid test cartridge, and a light receiving portion may receive light passed through the fluid test cartridge to measure an optical sensitivity. A concentration of the first material which is a target material in the fluid sample may be measured through the optical sensitivity measured by the detector. The optical sensitivity may include at least one of absorbance, luminescence, and fluorescence sensitivity. The optical sensitivity may also be referred to as an optical measurement value.

In addition, the fluid test cartridge may include a first chamber and a second chamber, wherein the first chamber may contain a first drying reagent and the second chamber may contain a second drying reagent. Since a concentration of a second material of the first drying reagent may be different from a concentration of a second material of the second drying reagent, a plurality of optical sensitivities may be measured for a fluid sample. As a result, a concentration of a fluid sample may be measured over a wider range.

Although the exemplary embodiments of the disclosure have been provided for illustrative purposes, those skilled in the art will appreciate that various modifications are possible, without departing from the scope and spirit of the disclosure as disclosed in the accompanying claims.

The terms used in the present specification are merely used to describe particular embodiments, and are not intended to limit the present disclosure. An expression used in the singular encompasses the expression of the plural, unless it has a clearly different meaning in the context. In the present specification, it is to be understood that the terms such as "including" or "having," etc., are intended to indicate the existence of the features, numbers, operations, components, parts, or combinations thereof disclosed in the specification, and are not intended to preclude the possibility that one or more other features, numbers, operations, components, parts, or combinations thereof may exist or may be added.

It will be understood that, although the terms "first", "second", etc., may be used herein to describe various elements, these elements should not be limited by these terms. The above terms are used only to distinguish one component from another. For example, a first component discussed below could be termed a second component, and similarly, a second component may be termed a first component without departing from the teachings of this disclosure. As used herein, the term "and/or" includes any and all combinations of one or more of the associated listed items.

In addition, the terms "unit", "device," "block", "member", and "module" used herein refer to a unit which can be embodied as software stored in memory, hardware such as field-programmable gate array (FPGA) or application specific integrated circuit (ASIC), or a combination thereof, for processing at least one function and performing an operation. However, the terms "unit", "device," "block", "member", and "module" are not limited to software or hardware. The "unit", "device," "block", "member", and "module" may be stored in storage medium and implemented by one or more processors.

Although embodiments of the present disclosure have been described, various changes and modifications may be made to the embodiments. It is intended that the present disclosure encompass such changes and modifications as fall within the scope of the appended claims.

What is claimed is:

1. A fluid test apparatus comprising:
   a housing;
   a fluid test cartridge that is accommodated in the housing, the fluid test cartridge including an array of chambers configured to accommodate a fluid sample and a drying reagent;
   a light emitter configured to emit light towards the array of chambers;
   a light sensor configured to receive the light incident on the array of chambers and to detect an optical property of a first material included in the fluid sample based on the received light; and
   a processor capable of determining a concentration of the first material based on the optical property detected by the light sensor,
   wherein the drying reagent includes a non-metallic particle bound to a second material that specifically binds to the first material,
   wherein the non-metallic particle is a nano-sized particle, and the nano-sized particle is at least one element selected from the group consisting of a carbon nanoparticle, a ceramic nanoparticle, and a polymeric nanoparticle, and
   wherein the non-metallic particle absorbs an entire wavelength of visible light,
   wherein the array of chambers comprises a first chamber which accommodates a first drying reagent, and a second chamber which accommodates a second drying reagent, and
   wherein the first drying reagent comprises a first amount of an internal standard material included in the fluid sample and the second drying reagent comprises a second amount of the internal standard material included in the fluid sample,
   wherein a first concentration of the first amount of the internal standard material, and a second concentration of the second amount of the internal standard material are preset, and the preset concentrations are mapped to identification information associated with the fluid test cartridge,
   wherein the second material of the first drying reagent is different from the second material of the second drying reagent such that the first drying reagent measures a first concentration of the first material, and the second drying reagent measures a second concentration of the first material different from the first concentration, and
   wherein the first material is antigens, and the second material is antibodies.

2. The fluid test apparatus of claim 1, wherein the non-metallic particle comprises at least one of a single particle or a combination of particles.

3. The fluid test apparatus of claim 1, wherein the ceramic nanoparticle is at least one element selected from the group consisting of glass and nano-silica.

4. The fluid test apparatus of claim 1, wherein the polymeric nanoparticle is at least one element selected from the group consisting of polymethyl methacrylate, polystyrene, cellulose, latex, hydrogel, and agarose.

5. The fluid test apparatus of claim 1, wherein the processor is further capable of determining concentration values of the first material over a plurality of wavelength bands of light received by the light sensor.

6. A fluid test cartridge comprising:
   an inlet through which a fluid sample is introduced;
   a tester configured to receive the fluid sample from the inlet and to test the fluid sample, wherein the tester comprises an array of chambers that accommodates the fluid sample introduced through the inlet and a drying reagent, the drying reagent including a nonmetallic particle bound to a second material that specifically binds to a first material included in the fluid sample,
   wherein the non-metallic particle is a nano-sized particle, and is at least one element selected from the group consisting of a carbon nanoparticle, a ceramic nanoparticle, and a polymeric nanoparticle, and
   wherein the non-metallic particle absorbs an entire wavelength of visible light, wherein the array of chambers comprises a first chamber which accommodates a first drying reagent, and a second chamber which accommodates a second drying reagent, and wherein the first drying reagent comprises a first amount of an internal standard material included in the fluid sample and the second drying reagent comprises a second amount of the internal standard material included in the fluid sample, wherein a first concentration of the first amount of the internal standard material, and a second concentration of the second amount of the internal standard material are preset, and the preset concentrations are mapped to identification information associated with the fluid test cartridge, wherein the second material of the first drying reagent is different from the second material of the second drying reagent such that the first drying reagent measures a first concentration of the first material, and the second drying reagent measures a second concentration of the first material different from the first concentration, and wherein the first material is antigens, and the second material is antibodies.

7. The fluid test cartridge of claim 6, wherein the non-metallic particle comprises at least one of a single particle or a combination of particles.

8. The fluid test cartridge of claim 6, wherein the ceramic nanoparticle is at least one element selected from the group consisting of glass and nano-silica.

9. The fluid test cartridge of claim 6, wherein the polymeric nanoparticle is at least one element selected from the group consisting of polymethyl methacrylate, polystyrene, cellulose, latex, hydrogel, and agarose.

10. A method for controlling a fluid test apparatus, the method comprising:
   Providing a fluid test apparatus comprising:
      a housing;
      a fluid test cartridge that is accommodated in the housing, the fluid test cartridge including an array of chambers configured to accommodate a fluid sample and a drying reagent;
      a light emitter configured to emit light towards the array of chambers;
      a light sensor configured to receive the light incident on the array of chambers and to detect an optical property of a first material included in the fluid sample based on the received light; and
      a processor capable of determining a concentration of the first material based on the optical property detected by the light sensor, wherein the drying reagent includes a non-metallic particle bound to a second material that specifically binds to the first material, wherein the non-metallic particle is a nano-sized particle, and the nano-sized particle is at least one element selected from the group consisting of a carbon nanoparticle, a ceramic nanoparticle, and a polymeric nanoparticle, and wherein the non-metallic particle absorbs an entire wavelength of visible light, wherein the array of chambers comprises a first chamber which accommodates a first drying reagent, and a second chamber which accommodates a second drying reagent, and wherein the first drying reagent comprises a first amount of an internal standard material included in the fluid sample and the second drying reagent comprises a second amount of the internal standard material included in the fluid sample, wherein a first concentration of the first amount of the internal standard material, and a second concentration of the second amount of the internal standard material are preset, and the preset concentrations are mapped to identification information associated with the fluid test cartridge, wherein the second material of the first drying reagent is different from the second material of the second drying reagent such that the first drying reagent measures a first concentration of the first material, and the second drying reagent measures a second concentration of the first material different from the first concentration, and wherein the first material is antigens, and the second material is antibodies;

mounting the fluid test cartridge in a housing of the fluid test apparatus;

reacting the fluid sample with the first drying reagent and/or the second drying reagent; and analyzing a reaction in the fluid test cartridge by measuring an optical property of the first material with the light sensor.

11. The method for controlling the fluid test apparatus of claim 10, wherein the analyzing comprises measuring a first optical property in the first chamber with the light sensor, and measuring a second optical property in the second chamber with the light sensor.

* * * * *